United States Patent
Everett et al.

(10) Patent No.: US 9,885,682 B2
(45) Date of Patent: Feb. 6, 2018

(54) BIOSENSOR SYSTEMS AND RELATED METHODS FOR DETECTING ANALYTES IN AQUEOUS AND BIOLOGICAL ENVIRONMENTS

(71) Applicant: THE JOHNS HOPKINS UNIVERSITY, Baltimore, MD (US)

(72) Inventors: Allen Dale Everett, Glenwood, MD (US); Howard Katz, Owings Mills, MD (US); Kalpana Besar, Baltimore, MD (US); Weiguo Huang, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 485 days.

(21) Appl. No.: 14/362,227

(22) PCT Filed: Dec. 3, 2012

(86) PCT No.: PCT/US2012/067609
§ 371 (c)(1),
(2) Date: Jun. 2, 2014

(87) PCT Pub. No.: WO2013/082600
PCT Pub. Date: Jun. 6, 2013

(65) Prior Publication Data
US 2014/0349005 A1    Nov. 27, 2014

Related U.S. Application Data

(60) Provisional application No. 61/566,076, filed on Dec. 2, 2011.

(51) Int. Cl.
*A61B 5/1486* (2006.01)
*G01N 33/50* (2006.01)
(Continued)

(52) U.S. Cl.
CPC ....... *G01N 27/327* (2013.01); *A61B 5/14507* (2013.01); *A61B 5/14865* (2013.01); *C23C 16/4486* (2013.01); *G01N 27/4145* (2013.01)

(58) Field of Classification Search
CPC .............................. A61B 5/1486; G01N 33/50
(Continued)

(56) References Cited

U.S. PATENT DOCUMENTS 5,846,814 A * 12/1998 Galla ..................... C12Q 1/002
                                                          204/403.06
6,127,183 A * 10/2000 Ivarsson .......... G01N 33/54373
                                                          356/445

(Continued)

FOREIGN PATENT DOCUMENTS

EP        2366994 A1     9/2011
EP    EP 2366994 A1 *    9/2011    ......... G01N 33/5438
(Continued)

OTHER PUBLICATIONS

Bystrenova et al. Neural Networks Grown on Organic Semiconductors. Advanced Function Materials. vol. 18. 2008.pp. 1751-1756.*

(Continued)

*Primary Examiner* — Cachet I Sellman
(74) *Attorney, Agent, or Firm* — Michael Best & Friedrich LLP; Jeffrey W. Childers

(57) ABSTRACT

Disclosed herein are biosensor systems and related methods for detecting analytes in aqueous and biologic environments. A biosensor system for detecting binding of an analyte of interest may include a detector configured to detect a change in an electrical property on a surface thereof. The detector may be a FET. The system also may include a passive layer disposed on a top surface of the detector. Further, the system may include a hydrophobic layer disposed on the passive (Continued)

US 9,885,682 B2

Page 2 layer. The system also may include a receptor-attachment material configured for binding to an analyte. A receptor may bind to the analyte, and the receptor may be attached to the receptor-attachment material. The binding of the analyte to the receptor can cause the change of the electrical property at the surface. In response to the change for example, a current may change for indicating the binding of the analyte to the receptor.

62 Claims, 15 Drawing Sheets

(51) Int. Cl.
G01N 27/327 (2006.01)
G01N 27/414 (2006.01)
A61B 5/145 (2006.01)
C23C 16/448 (2006.01)

(58) Field of Classification Search
USPC ............ 427/2.13, 2.11; 600/345, 309
See application file for complete search history.

(56) References Cited

U.S. PATENT DOCUMENTS

| | | | | |
|---|---|---|---|---|
| 6,372,425 | B1* | 4/2002 | Arnold | C07K 16/1063 435/235.1 |
| 8,158,353 | B2* | 4/2012 | Bulte | C12Q 1/6881 435/6.12 |
| 2005/0123680 | A1 | 6/2005 | Kang | |
| 2006/0148167 | A1* | 7/2006 | Brown | B82Y 10/00 438/232 |
| 2008/0204043 | A1* | 8/2008 | Wang | B82Y 15/00 324/633 |
| 2008/0249385 | A1 | 10/2008 | Phan | |
| 2009/0326344 | A1 | 12/2009 | Meyer | |
| 2012/0071342 | A1* | 3/2012 | Lochhead | G01N 21/6452 506/9 |
| 2013/0071289 | A1* | 3/2013 | Knoll | G01N 33/5438 422/69 |
| 2013/0138359 | A1* | 5/2013 | Armstrong | H03H 5/003 702/23 |

FOREIGN PATENT DOCUMENTS

| | | |
|---|---|---|
| WO | 2003005890 A2 | 1/2003 |
| WO | 2004078252 A2 | 9/2004 |

OTHER PUBLICATIONS

Khan et al. Effect of Passivation on the sensitivity and stability of pentacene transistor sensors in aqueous media. Biosensors and Bioelectronics. vol. 26. 2011. pp. 4217-4221.*
Kim et al (2010) Direct label-free electrical immunodetection in human serum using a flow-through-apparatus approach with integrated field-effect transistors. Biosens Bioelectron. Mar. 15, 2010;25(7):1767-73. doi: 10.1016/j.bios.2009.12.026. Epub Dec. 29, 2009.
Roberts et al (2008) Water-stable organic transistors and their application in chemical and biological sensors. Proc Natl Acad Sci U S A. Aug. 26, 2008;105(34):12134-9. doi: 10.1073/pnas.0802105105. Epub Aug. 18, 2008.
Yoo et al (2011) Bead packing and release using flexible polydimethylsiloxane membrane for semi-continuous biosensing. Artif Organs. Jul. 2011;35(7):E136-44. doi: 10.1111/j.1525-1594.2011.01240.x. Epub Jun. 9, 2011.
Della Ciana et al (1996) Robust, reliable biosensor for continuous monitoring of urea during dialysis. Clin Chem. Jul. 1996;42(7):1079-85.
Thavarungkul et al (1991) Continuous monitoring of urea in blood during dialysis. Biosens Bioelectron. 1991;6(2):101-7.
Savage et al (2011) Plasma glial fibrillary acidic protein levels in a child with sickle cell disease and stroke. Acta Haematol. 2011;125(3):103-6. doi: 10.1159/000321791. Epub Nov. 24, 2010.
Savage et al (2011) Plasma glial fibrillary acidic protein levels in children with sickle cell disease. Am J Hematol. May 2011;86(5):427-9. doi: 10.1002/ajh.21995.
Bembea et al (2011) Glial fibrillary acidic protein as a brain injury biomarker in children undergoing extracorporeal membrane oxygenation. Pediatr Crit Care Med. Sep. 2011;12(5):572-9. doi: 10.1097/PCC.0b013e3181fe3ec7.
Styles et al (1996) Phospholipase A2 levels in acute chest syndrome of sickle cell disease. Blood. Mar. 15, 1996;87(6):2573-8.
Naprawa et al (2005) Serum biomarkers for identifying acute chest syndrome among patients who have sickle cell disease and present to the emergency department. Pediatrics. Sep. 2005;116(3):e420-5. Epub Aug. 11, 2005.
Bargoma et al (2005) Serum C-reactive protein parallels secretory phospholipase A2 in sickle cell disease patients with vasoocclusive crisis or acute chest syndrome. Blood. Apr. 15, 2005;105(8):3384-5.
Styles et al (2007) Transfusion prevents acute chest syndrome predicted by elevated secretory phospholipase A2. Br J Haematol Jan. 2007;136(2):343-4. Epub Nov. 30, 2006.
Andropoulos et al (2010) Brain immaturity is associated with brain injury before and after neonatal cardiac surgery with high-flow bypass and cerebral oxygenation monitoring. J Thorac Cardiovasc Surg. Mar. 2010;139(3):543-56. doi: 10.1016/j.jtcvs.2009.08.022. Epub Nov. 11, 2009.
Ennen et al (2011) Glial fibrillary acidic protein as a biomarker for neonatal hypoxic-ischemic encephalopathy treated with whole-body cooling. Am J Obstet Gynecol. Sep. 2011;205(3):251.e1-7. doi: 10.1016/j.ajog.2011.06.025. Epub Jun. 15, 2011.
Cao et al (2012) Ultrasensitive luminol electrochemiluminescence for protein detection based on in situ generated hydrogen peroxide as coreactant with glucose oxidase anchored AuNPs@MWCNTs labeling. Biosens Bioelectron. Jan. 15, 2012;31(1):305-9. doi: 10.1016/j.bios.2011.10.036. Epub Oct. 25, 2011.
Ren et al (2012) Increased detection of human cardiac troponin I by a decrease of nonspecific adsorption in diluted self-assembled monolayers. Appl Surf Sci 258:5230-7.
Jensen et al (2011) Inkjet-printed gold nanoparticle electrochemical arrays on plastic. Application to immunodetection of a cancer biomarker protein. Phys Chem Chem Phys. Mar. 21, 2011;13(11):4888-94. doi: 10.1039/c0cp01755h. Epub Jan. 7, 2011.
Tang et al (2012) Fabrication of immunosensor microwell arrays from gold compact discs for detection of cancer biomarker proteins. Lab Chip. Jan. 21, 2012;12(2):281-6. doi: 10.1039/c1lc20833k. Epub Nov. 24, 2011.
Dou et al (2012) Voltammetric Immunoassay for the Detection of Protein Biomarkers. Electroanalysis 24:264-272.
Mao et al (2012) Label-free electrochemical immunosensor based on graphene/methylene blue nanocomposite. Anal Biochem. Mar. 1, 2012;422(1):22-7. doi: 10.1016/j.ab.2011.12.047. Epub Jan. 8, 2012.
Lee et al (2012) Electrochemical detection of high-sensitivity CRP inside a microfluidic device by numerical and experimental studies. Biomed Microdevices. Apr. 2012;14(2):375-84. doi: 10.1007/s10544-011-9614-7.
Reyes et al (2011) ZnO thin film transistor immunosensors with high sensitivity and selectivity. Applied Physics Letters 98:173702.
Hideshima et al (2011) Fabrication of stable antibody-modified field effect transistors using electrical activation of Schiff base cross-linkages for tumor marker detection. Biosens Bioelectron. Jan. 15, 2011;26(5):2419-25. doi: 10.1016/j.bios.2010.10.023. Epub Oct. 20, 2010.
Shalev et al (2012) The interplay between pH sensitivity and label-free protein detection in immunologically modified nano-scaled field-effect transistor. Biosens Bioelectron. Jan. 15, 2012;31(1):510-5. doi: 10.1016/j.bios.2011.11.038. Epub Dec. 2, 2011.

(56) References Cited

OTHER PUBLICATIONS

Huang et al (2007) Hydroxy-terminated organic semiconductor-based field-effect transistors for phosphonate vapor detection J Am Chem Soc. Aug. 1, 2007;129(30):9366-76. Epub Jul. 11, 2007.

Huang et al (2008) Monolayer-dimensional 5,5'-Bis(4-hexylphenyl)-2,2'-bithiophene transistors and chemically responsive heterostructures. Advanced Materials 20:2567.

See et al (2007) Enhanced Response of n-Channel Naphthalenetetracarboxylic Diimide Transistors to Dimethyl Methylphosphonate Using Phenolic Receptors. Advanced Materials 19:3322.

Someya et al (2002) Integration and response of organic electronics with aqueous microfluidics. Langmuir 18:5299.

Khan et al (2010) In Situ, Label-Free DNA Detection Using Organic Transistor Sensors. Adv Mater 22(40):4452.

Khan et al (2011) Pentacene based Organic Thin Film Transistors as the Tranducer for Biochemical Sensing in Aqueous Media. Chemistry of Materials 23:1946.

Lin et al (2012) Organic Thin-Film Transistors for Chemical and Biological Sensing. Advanced Materials 24(1):34.

Kergoat et al (2012) Advances in organic transistor-based biosensors: from organic electrochemical transistors to electrolyte-gated organic field-effect transistors. Anal Bioanal Chem. Feb. 2012;402(5):1813-26. doi: 10.1007/s00216-011-5363-y. Epub Sep. 11, 2011.

Tremblay et al (2011) Digital Inverter Amine Sensing via Synergistic Responses by n and p Organic Semiconductors. Adv Funct Mater. Nov. 22, 2011;21(22):4314-4319.

Dhar et al (2011) Threshold voltage shifting for memory and tuning in printed transistor circuits . Materials Science & Engineering R-Reports 72(4):49

International Search Report and Written Opinion dated Mar. 28, 2013 from PCT International Application No. PCT/US2012/067609.

Khan et al., In situ antibody detection and charge discrimination using aqueous stable pentacene transistor biosensors, J. Am. Chem. Soc., Jan. 31, 2011, vol. 133, No. 7, pp. 2170-2176.

Khan et al., Effect of passivation on the sensitivity and stability of pentacene transistor sensors in aqueous media, Biosens. and Bioelectron., Apr. 2, 2011, vol. 26, No. 10, pp. 4217-4221.

\* cited by examiner

BIOSENSOR SYSTEMS AND RELATED METHODS FOR DETECTING ANALYTES IN AQUEOUS AND BIOLOGICAL ENVIRONMENTS

CROSS REFERENCE TO RELATED APPLICATIONS

This application is a 35 U.S.C. § 371 U.S. national phase entry of International Application No. PCT/US2012/067609 having an international filing date of Dec. 3, 2012, which claims the benefit of U.S. Provisional Application No. 61/566,076, filed Dec. 2, 2011. The content of each of the aforementioned applications is herein incorporated by reference in its entirety.

BACKGROUND

The care of ill patients would be facilitated by continuous monitoring of drug levels, drug effects and biomarkers of the clinical state. An example is monitoring acute organ injury biomarkers, such as the central nervous system (CNS), and effects of anticoagulation drugs during cardiac surgery. Other examples include, but are not limited to, general surgery, trauma, dialysis, sepsis, invasive non-surgical procedures (e.g., cardiac catheterization and ablations), and the like. CNS injury is common after cardiac surgery occurring in at least 36% of neonates, D. B. Andropoulos, et al., *Brain Immaturity is Associated with MRI Brain Injury Before and After Neonatal Cardiac Surgery with High-Flow Bypass and Cerebral Oxygenation Monitoring*, J Thorac Cardiovasc Surg. 2010 March; 139(3): 543-556, and 1.4-6% of adults have neurologic side effects.

In adults, evidence of post-operative CNS injury is associated with 3-4 fold increased risk of death and major morbidity. Unfortunately, therapies to decrease CNS injury during cardiac surgery are challenged by no objective measures to identify CNS injury as it is occurring. Current clinical assay platforms for measuring biomarkers are typically ELISA based and have a minimum assay time of 30 minutes, which although rapid, significantly limits the therapeutic window for treatment of CNS injury. Development of an electronic biosensor platform for continuous detection of CNS injury biomarkers would fill an important clinical void in cardiac surgery to monitor patients at risk for CNS injury rapidly and easily. The ability of continuous monitoring of blood for brain injury biomarker levels would allow timely intervention, development of new therapies and provide benchmarks for comparing the effectiveness of new therapies.

An example of a brain injury biomarker is glial fibrillary acidic protein (GFAP), an astrocycle specific protein, whose presence in blood is associated with brain injury, and in children with birth asphyxia, C. S. Ennem, et al., *Glial Fibrillary Acidic Protein as a Biomarker for Neonatal Hypoxic-Ischemic Encephalopathy Treated with Total Body Cooling*, Am J Obstet Gynecol, 205:251, (2011), and extracorporeal membrane oxygenation support. M. M. Bembea, et al., *Glial fibrillary acidic protein as a brain injury biomarker in children undergoing extracorporeal membrane oxygenation*, Pediatr Crit. Care Med 12, 572 (2011). In addition, patients often require significant anticoagulation with drugs like heparin, for example, during cardiac surgery, to prevent blood clotting from exposure to the plastic surfaces if the cardiopulmonary bypass circuit and cannulas. Drugs like heparin require frequent measurements as they are rapidly metabolized, have a narrow therapeutic window and a dosing requirement with wide individual variability. The risks with under (embolic stroke) or over anticoagulation (hemorraghic stroke, subdural hematoma) result in significant mortality and morbidity. The ability to detect brain injury biomarkers and drugs like heparin in real time could dramatically increase their utility, improving patient care, procedure safety and outcomes.

SUMMARY

Disclosed herein are biosensor systems and related methods for detecting analytes in aqueous and/or biological environments. According to one aspect, a biosensor system for detecting binding of an analyte of interest may include a detector configured to detect a change in an electrical property on a surface thereof. In a representative, non-limiting example, the detector may be a field effect transistor. The system also may include a passive layer disposed on a top surface of the detector. In an example, the passive layer may be a fluoropolymer. Further, the system may include a hydrophobic layer disposed on the passive layer. The hydrophobic layer may be, for example, a vapor-deposited hydrophobic material. The system also may include a receptor-attachment material disposed on the hydrophobic layer and configured for binding to an analyte. One or more receptors may bind to the analyte, and the one or more receptors may be attached to the receptor-attachment material. In an example, the detector may be positioned in a biological environment for detecting proteins, such as blood flowing in blood or urine. In another example, the detector may detect non-protein molecules such as metabolites and drugs. The binding of the analyte to the one or more receptors can cause the change of the electrical property at the surface. In response to the change for example, a current may change for indicating the binding of the analyte to the one or more receptors.

According to another aspect, a method for manufacturing a biosensor may include providing a detector configured to detect a change in an electrical property on a surface thereof. For example, the detector may comprise a device selected from the group consisting of a field effect transistor, one or more carbon nanotubes, one or more silicon nanowires, a biochem-resistor, or a $SnO_2$ nanobelt. A passive layer may be disposed on a top surface of the detector. Further, a hydrophobic layer may be disposed on the passive layer. A receptor-attachment material may be disposed on the hydrophobic layer. The receptor-material may be configured to bind to an analyte. One or more receptors may be attached to the receptor-attachment material. The one or more receptors may be configured to bind to the analyte such that the electrical property at the surface changes.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
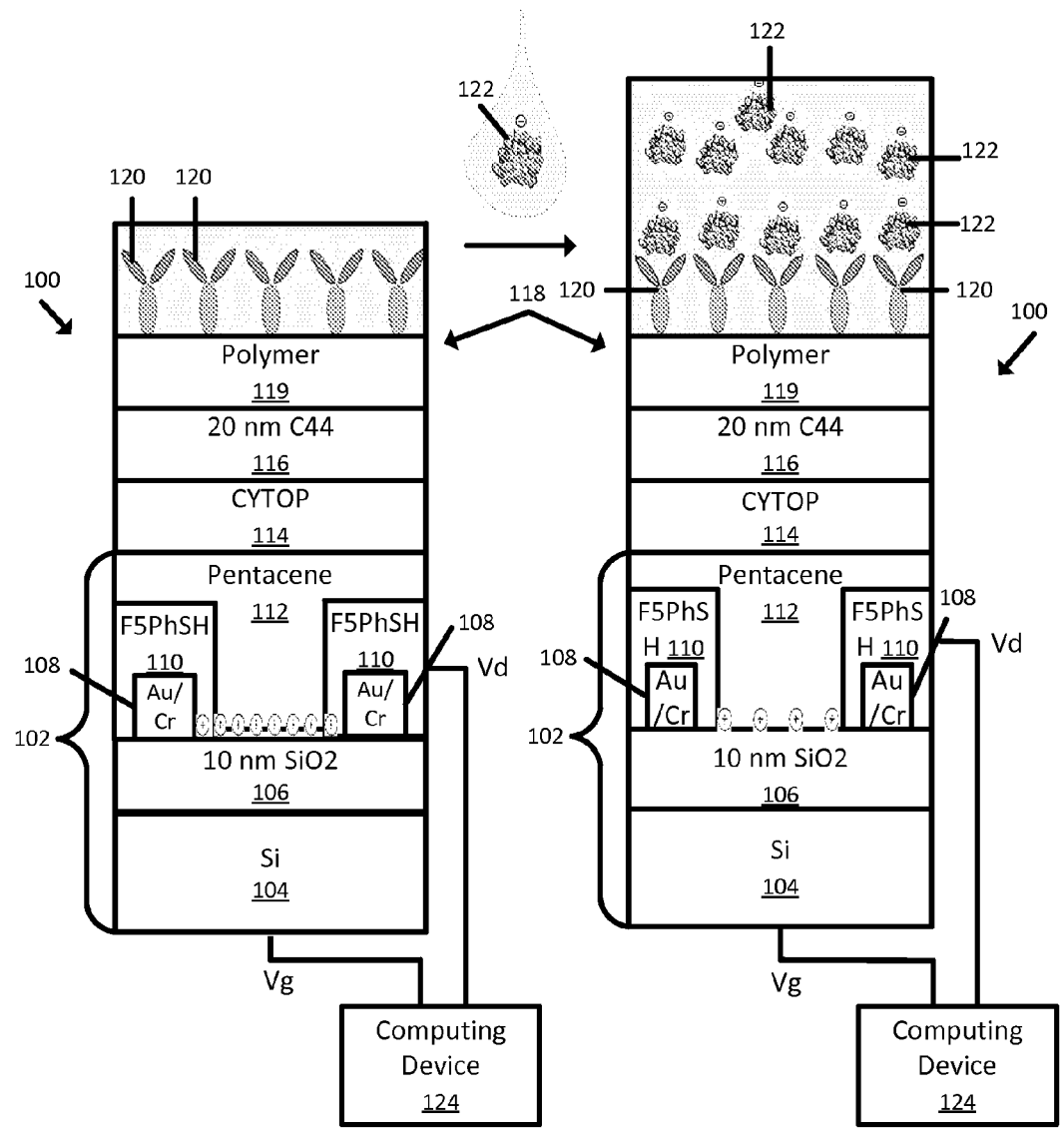
Figure 1B:
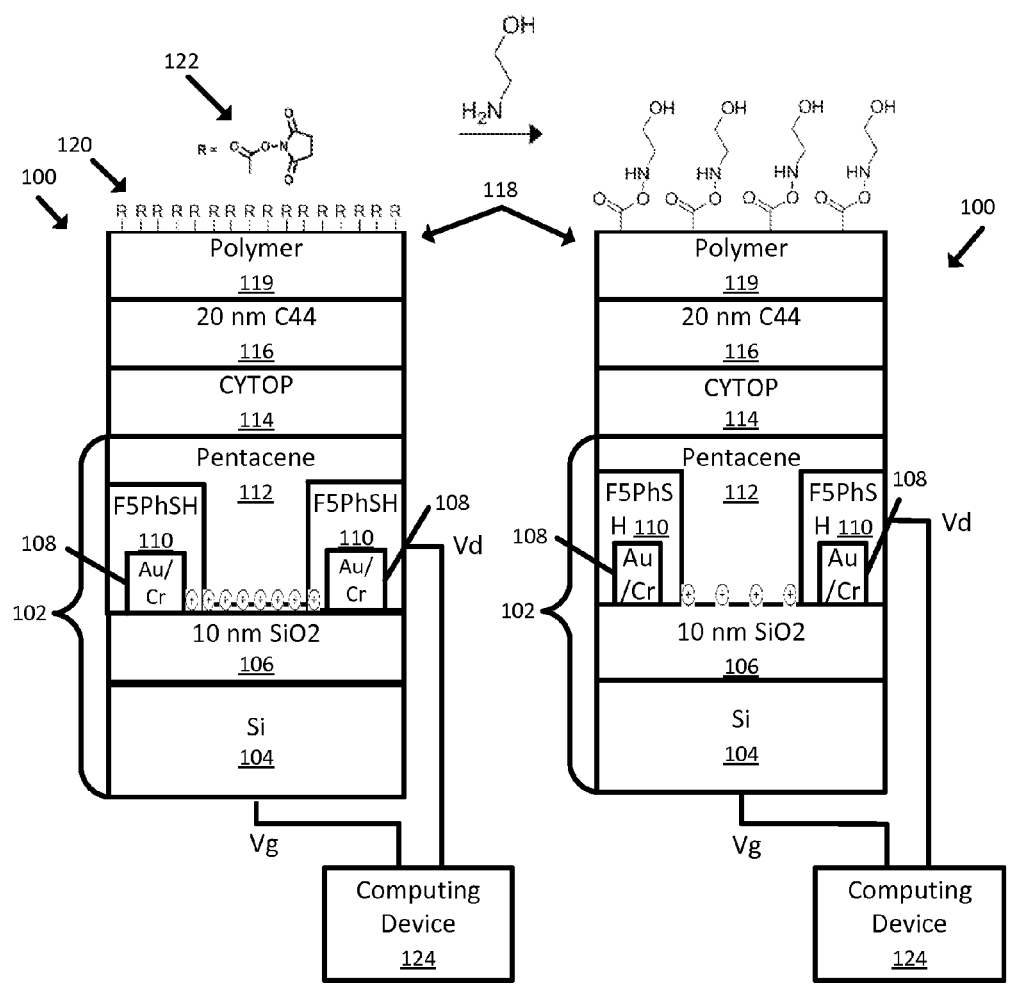
Figure 2:
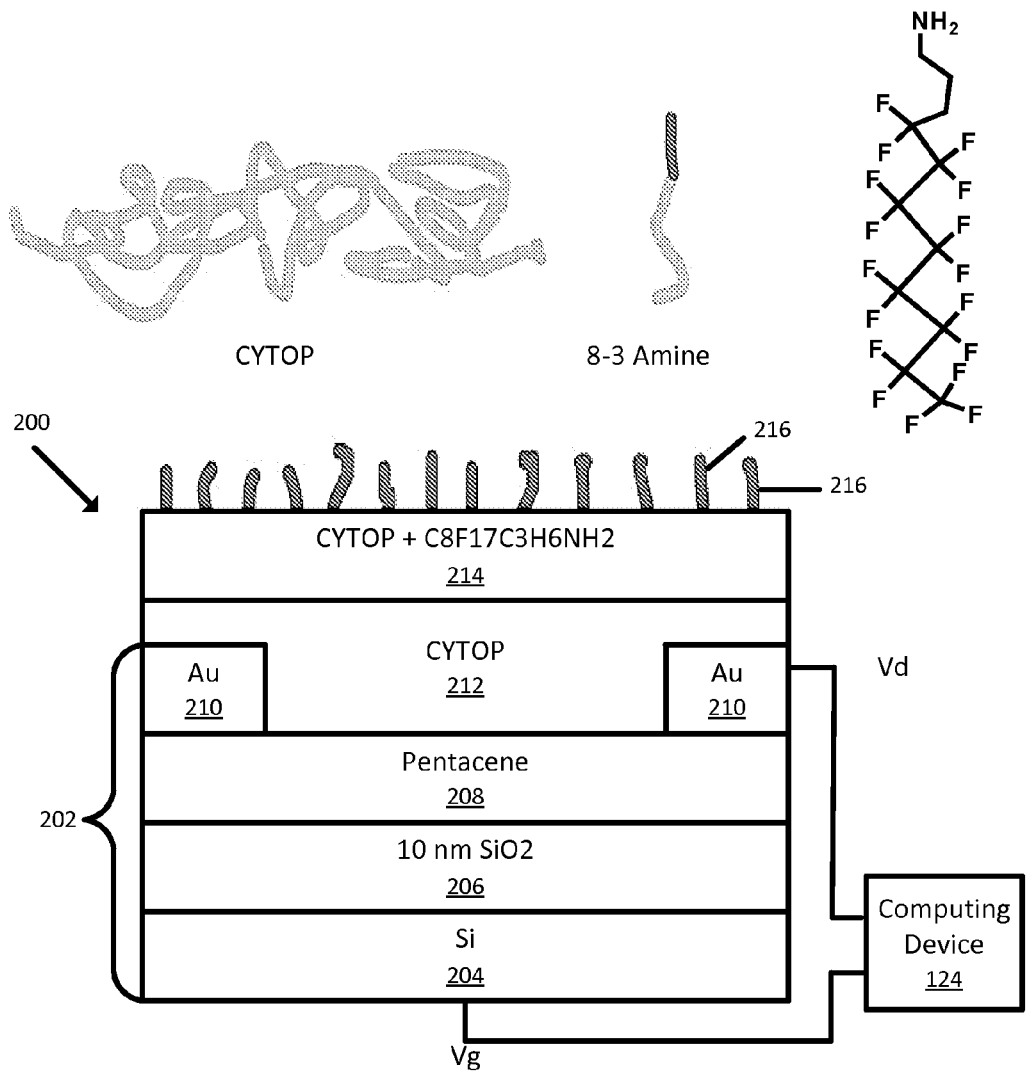
Figure 3:
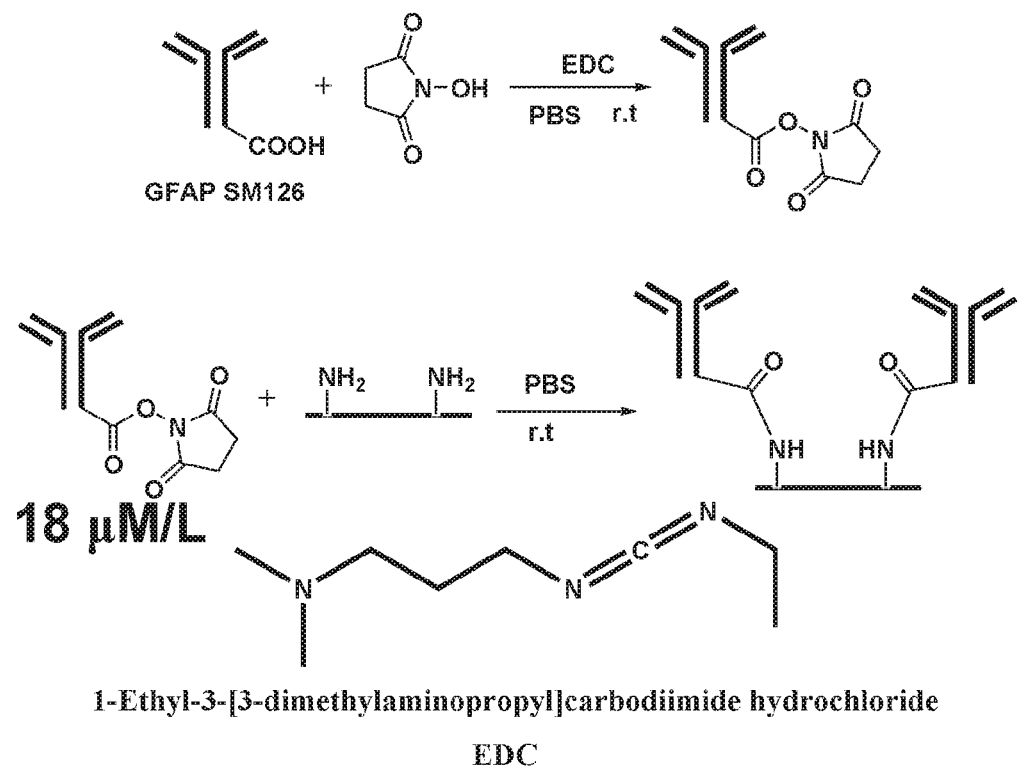
Figure 4:
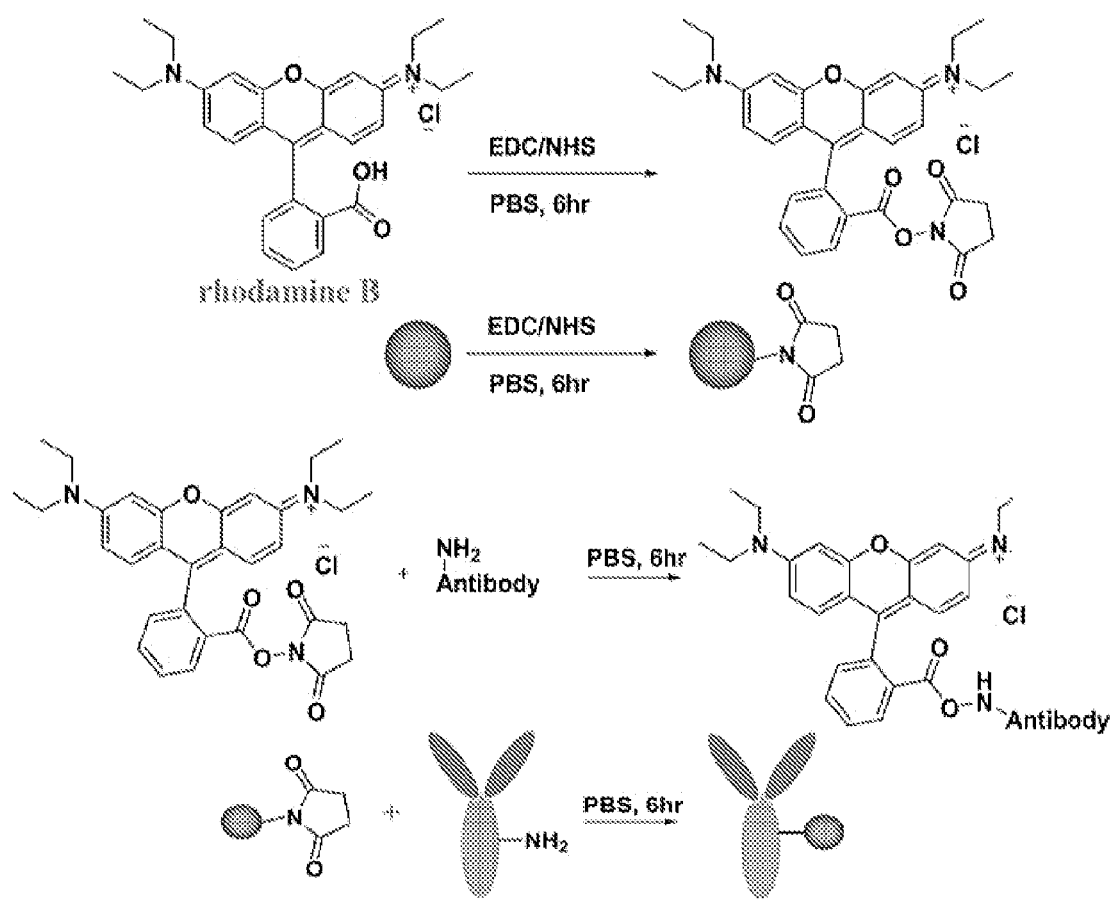
Figure 5:
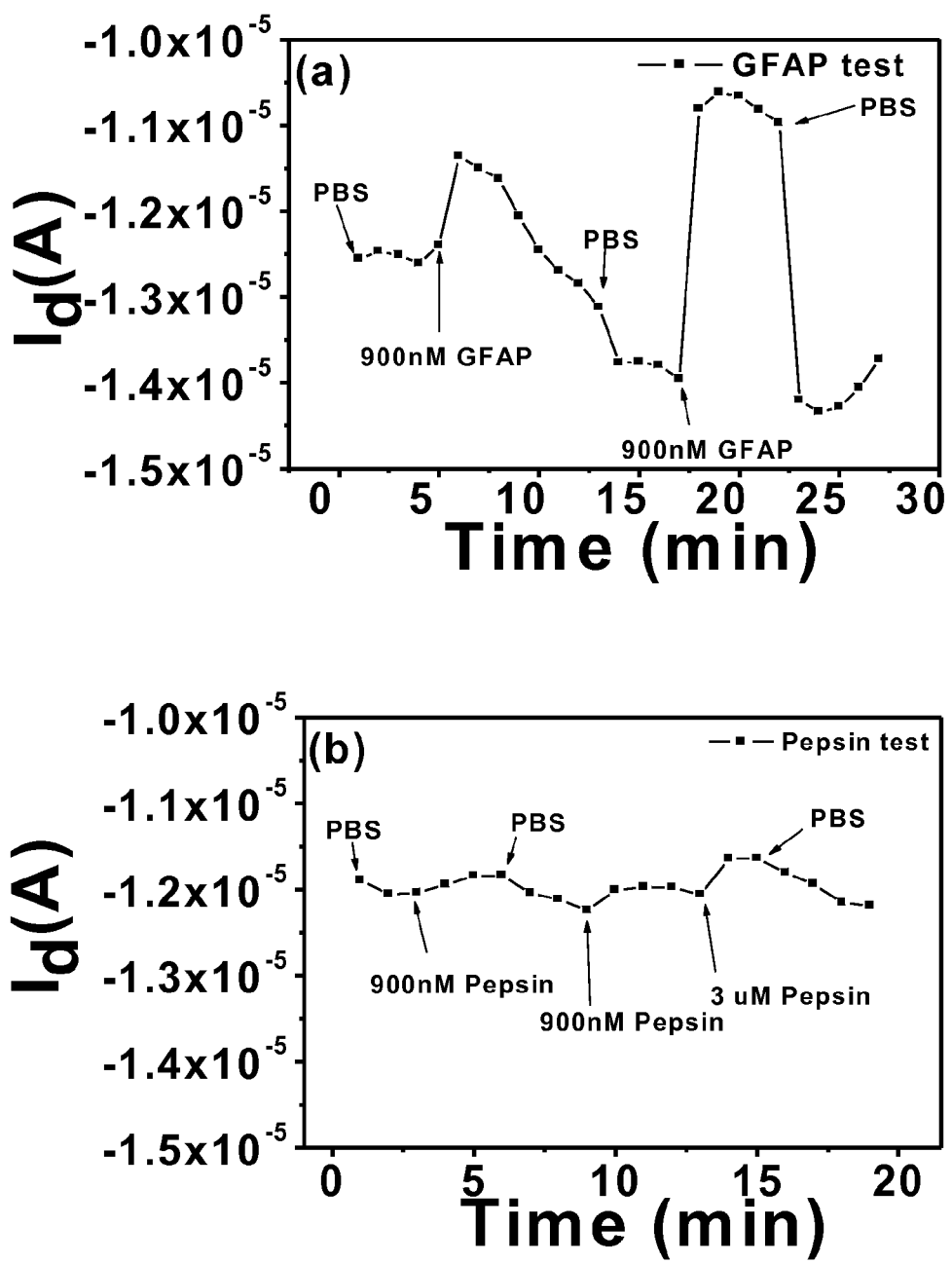
Figure 6:
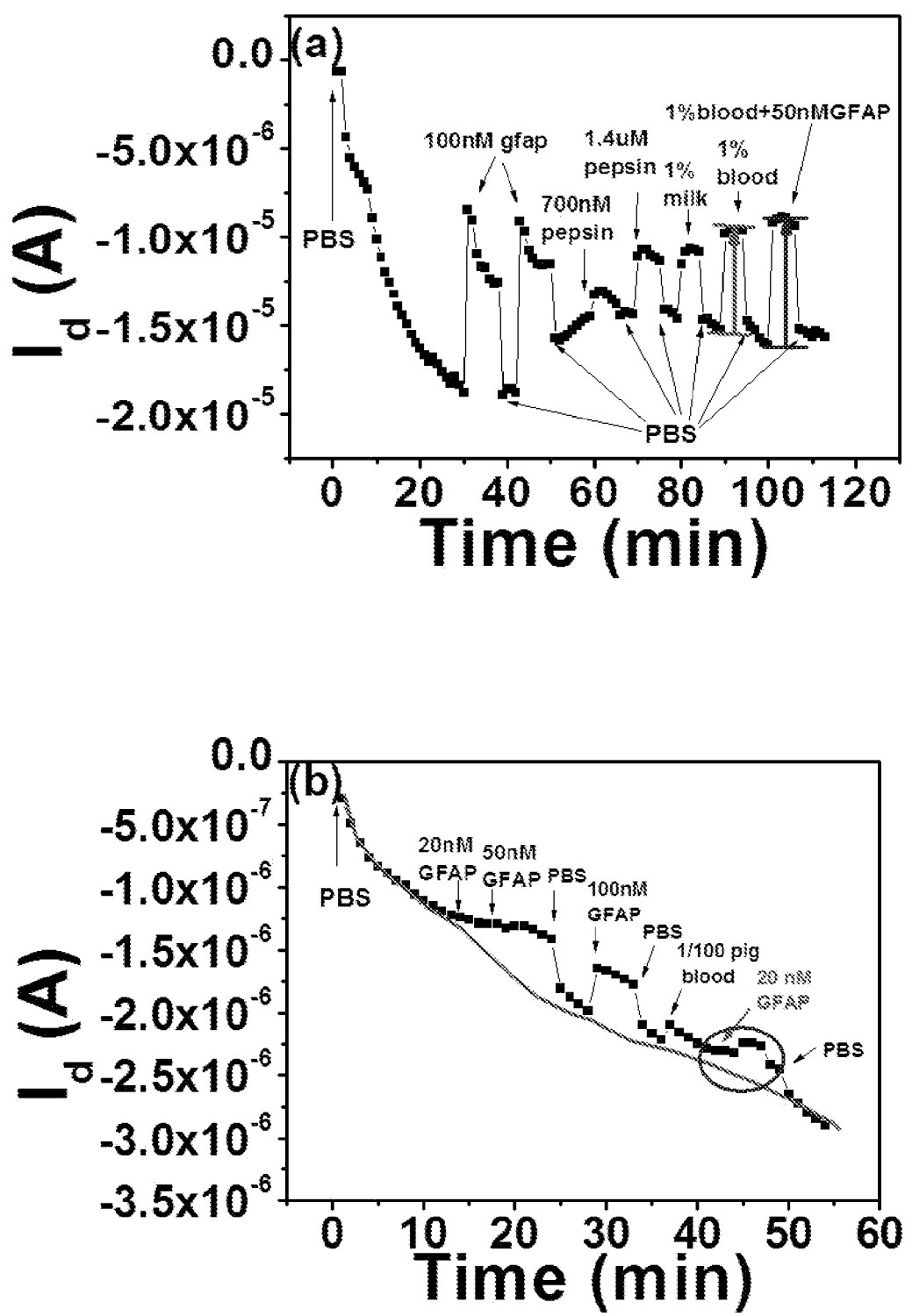
Figure 7:
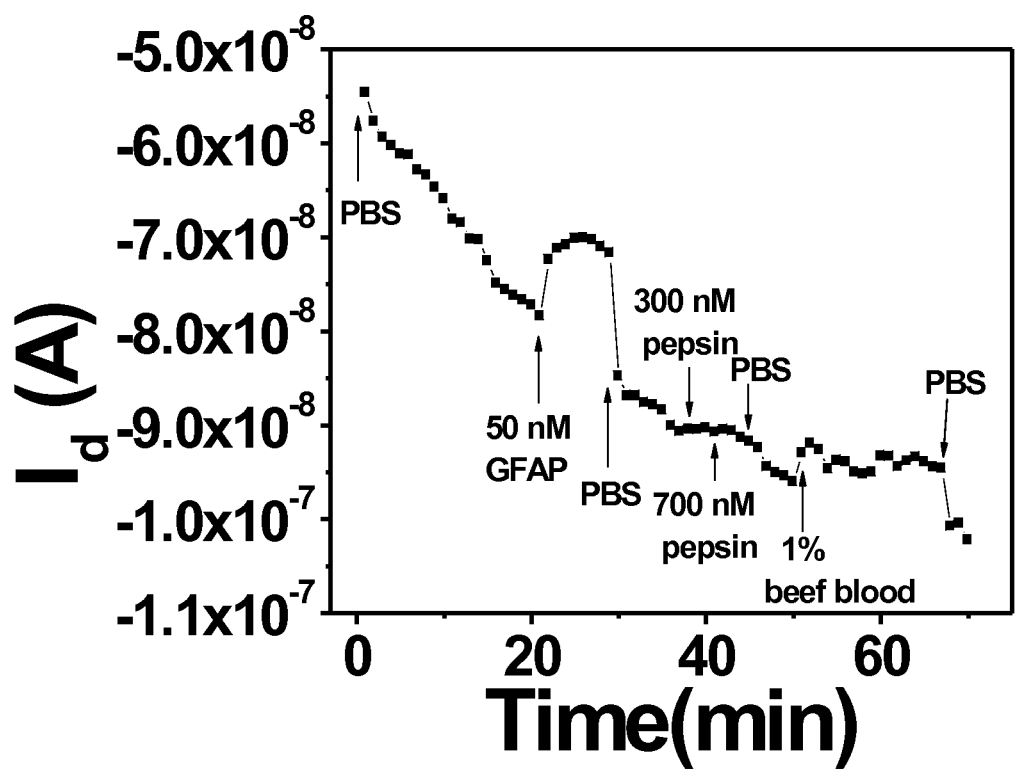
Figure 8:
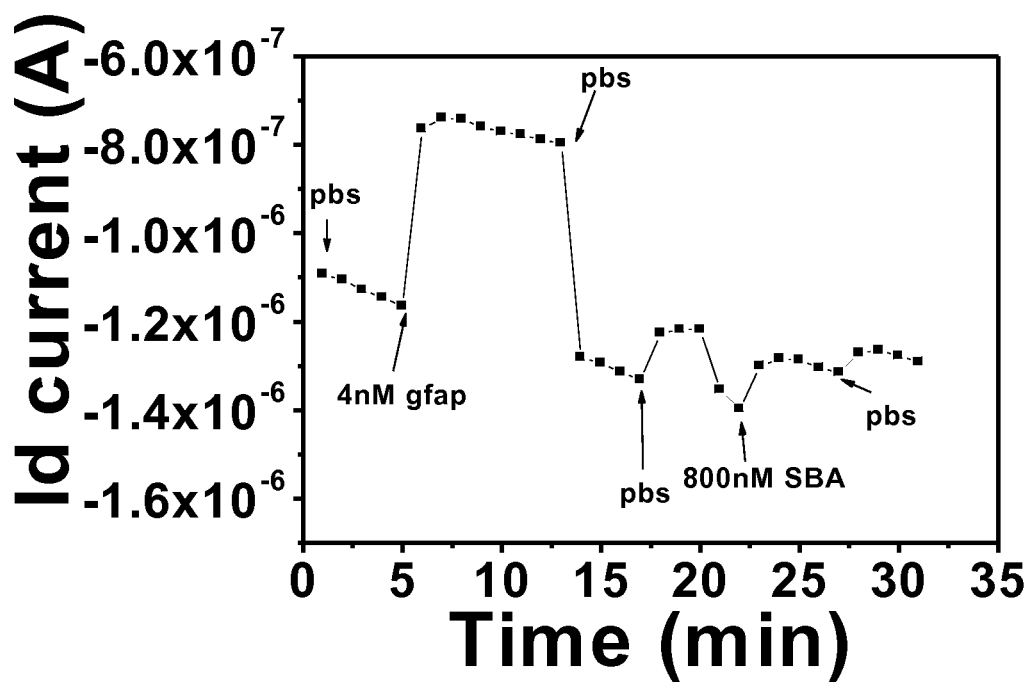
Figure 9:
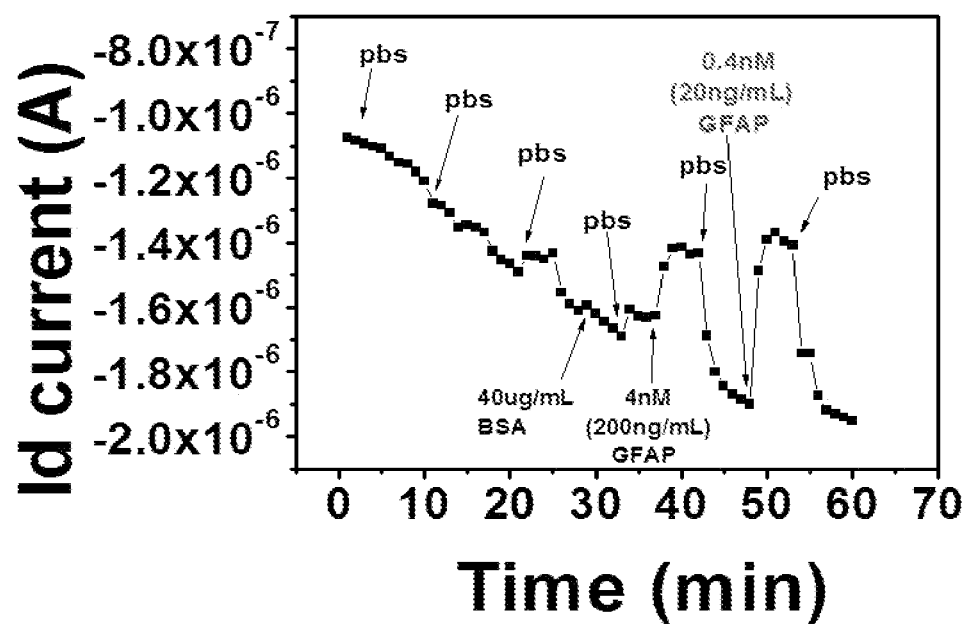
Figure 10:
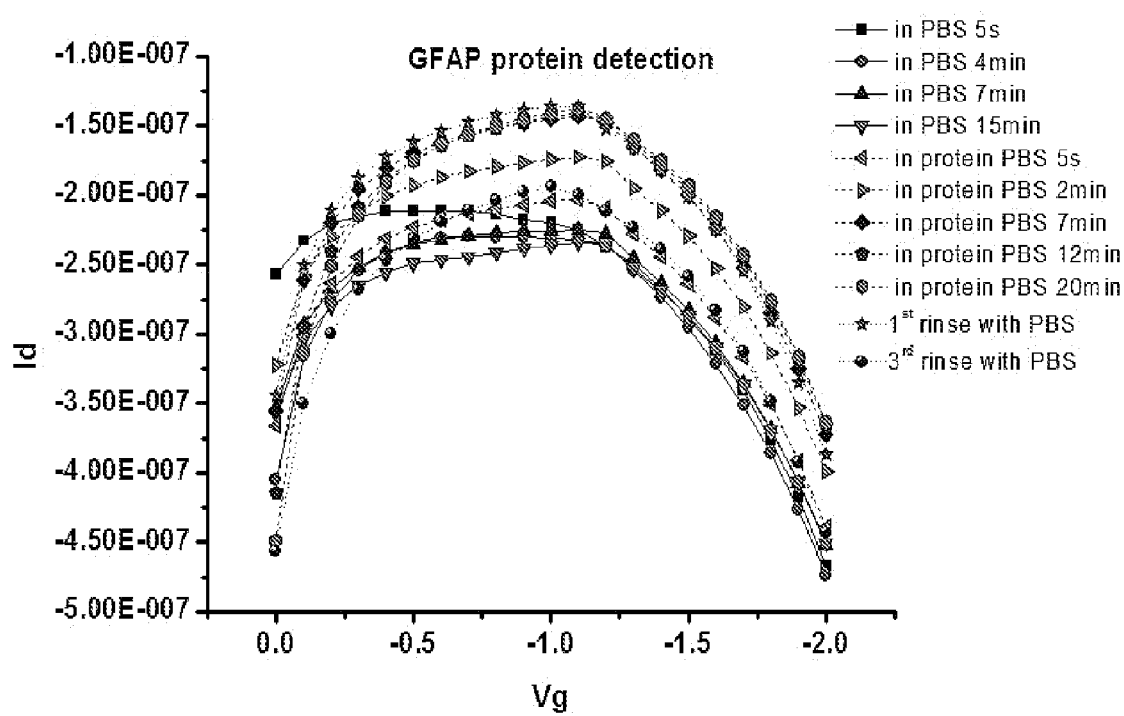
Figure 11:
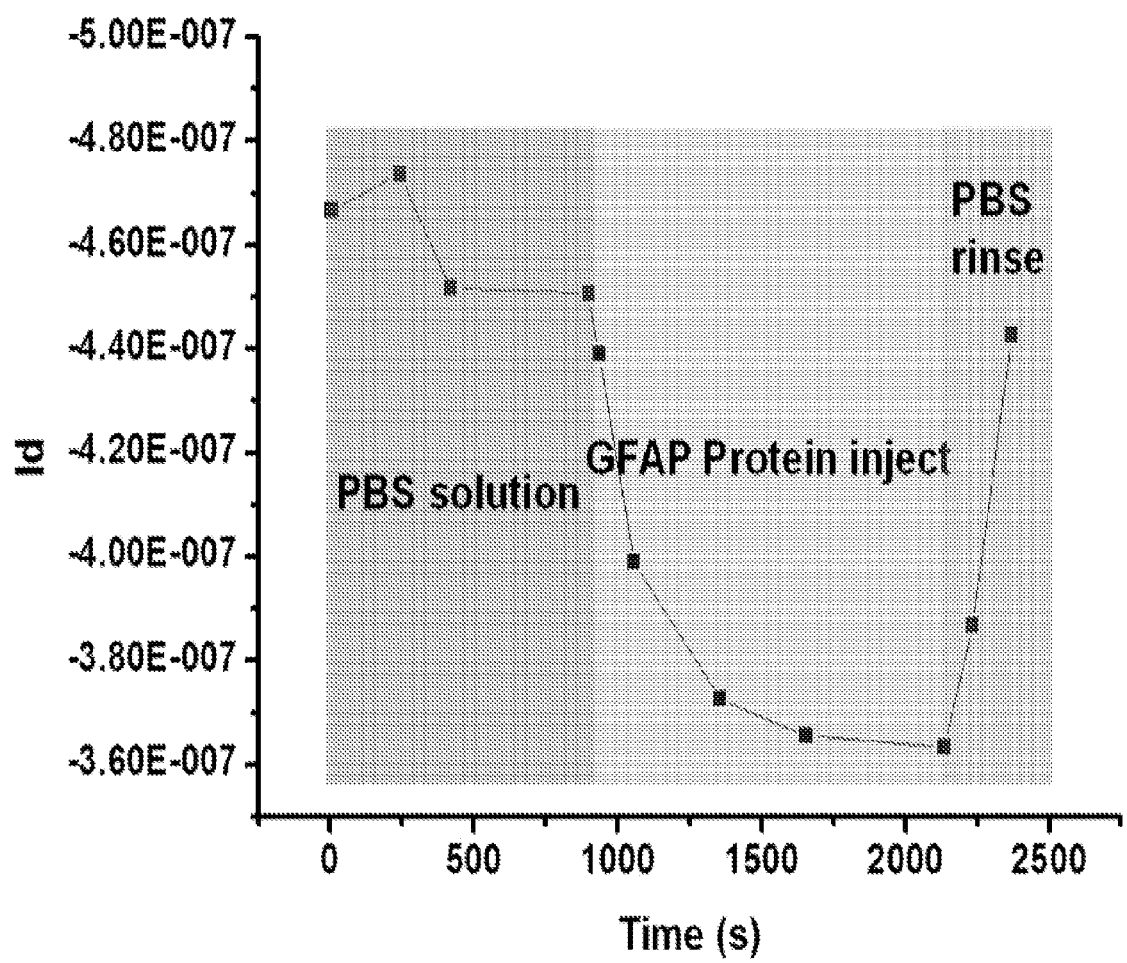
Figure 12:
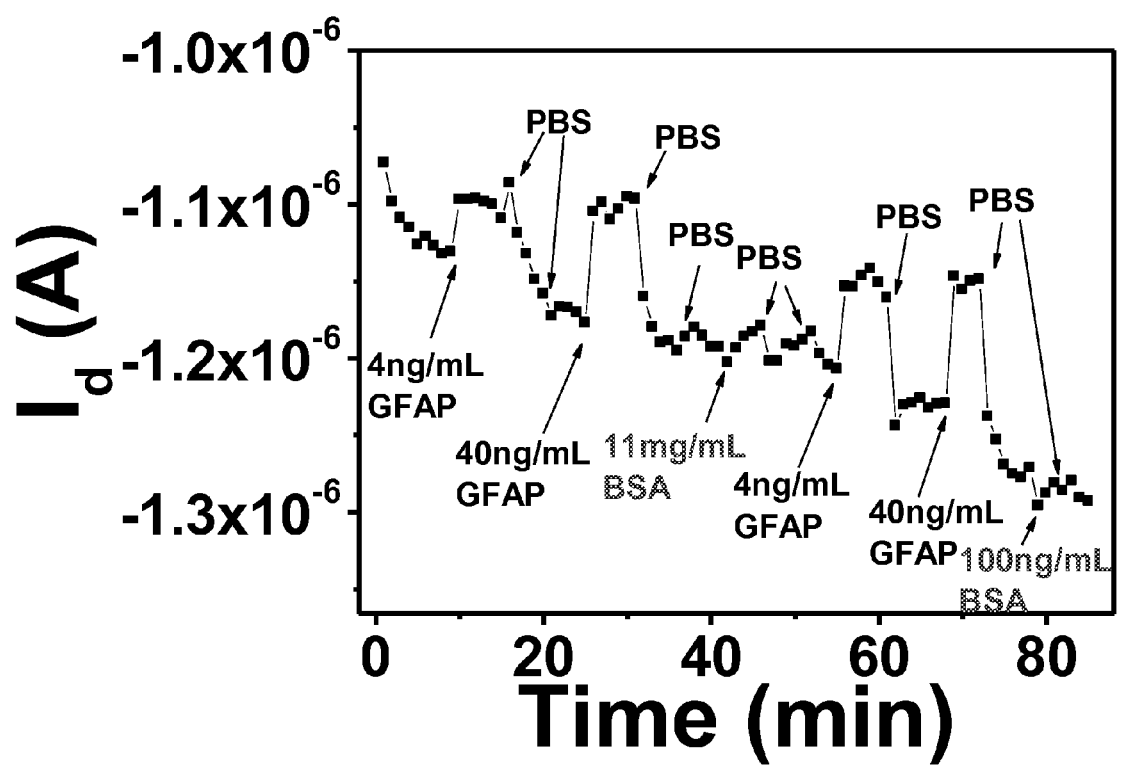
Figure 13:
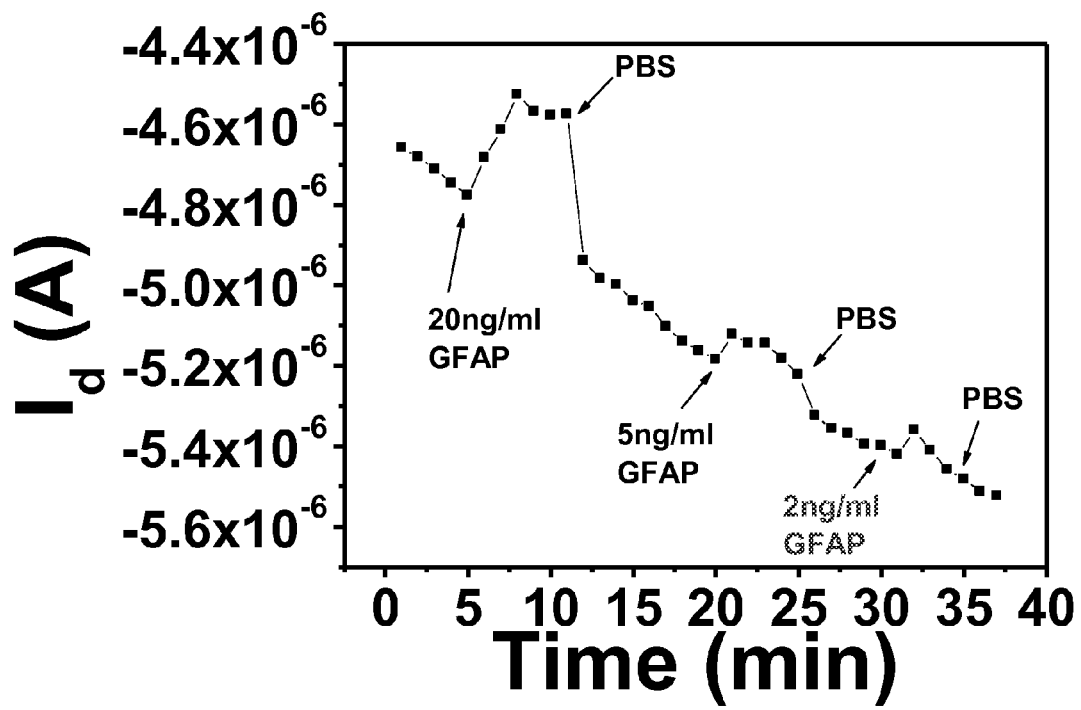
Figure 14:
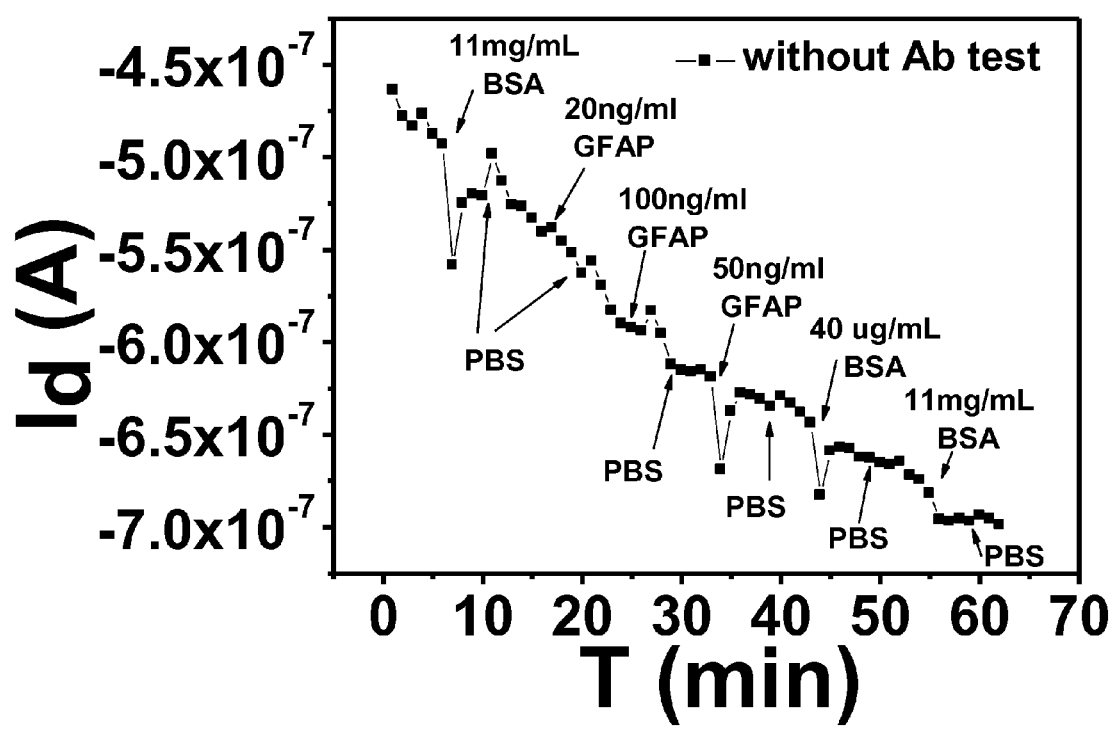

Having thus described the presently disclosed subject matter in general terms, reference will now be made to the accompanying Figures, which are not necessarily drawn to scale, and wherein:

FIG. 1A illustrates a diagram depicting an example biosensor system 100 operating in a process for detecting binding of an analyte of interest in accordance with embodiments of the present disclosure;

FIG. 1B illustrates a diagram depicting another example biosensor system 100 in accordance with embodiments of the present disclosure;

FIG. 2 illustrates a diagram depicting another example biosensor system 200 operating in a process for detecting binding of an analyte of interest in accordance with embodiments of the present disclosure;

FIG. 3 is a schematic diagram of a method for attaching a receptor to the receptor-attachment material on the biosensor in accordance with embodiments of the present disclosure;

FIG. 4 is a schematic diagram of the method used to label a receptor to determine its attachment to the biosensor in accordance with embodiments of the present disclosure;

FIGS. 5A and 5B are graphs of drain current versus time for the biosensor according to FIG. 1A in the presence of various substances: (A) Addition of 900 nM of the analyte GFAP at the surface of the biosensor results in a significant decrease in current which is restored by a PBS rinse; and (B) Addition of 900-nM pepsin at the surface of the biosensor does not significantly affect drain current;

FIGS. 6A and 6B are graphs of drain current versus time for the biosensor according to FIG. 1A in the presence of various substances to simulate real time detection of the analyte GFAP in blood: (A) Response of 50-nM to 100-nM of GFAP at the surface of the biosensor results in a significant decrease in drain current even in the presence of 1% blood or 1% milk; and (B) Addition of GFAP, PBS, and blood at the surface of the biosensor to determine the baseline of the response;

FIG. 7 is a graph of drain current versus time for the biosensor according to FIG. 1A in the presence of the analyte GFAP and other substances except that the biosensor in this experiment has a much thicker CYTOP® layer;

FIG. 8 is a graph of drain current versus time for the biosensor according to FIG. 1A in the presence of 4 nM of the analyte GFAP and 800-nM BSA as a control;

FIG. 9 is a graph of drain current versus time for the biosensor according to FIG. 1A in the presence of as little as 0.4 nM of the analyte GFAP and 40-µg/mL BSA as a control;

FIG. 10 is a graph showing drain current versus voltage in the presence of PBS or the analyte GFAP under different conditions;

FIG. 11 is a graph of drain current versus time when GFAP is provided at the surface of the biosensor following PBS and then a subsequent PBS rinse;

FIG. 12 shows a graph of drain current versus time when using a low GFAP concentration and high and broad BSA concentration;

FIG. 13 shows a graph of drain current versus time depicting a limit of detection of GFAP; and FIG. 14 shows a graph of drain current versus time for control sensing experiments using the system shown in FIG. 1B.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

A. Field Effect Transistors (FETs) as Biosensor Platforms: Overview

Field effect transistors (FETs) have been used as biosensor platforms, and can allow for real-time sensing of analytes, binary outputs, logic functions, and signal amplification. A biosensor is a device that desirably detects one or multiple analytes with adequate sensitivity in real time with minimal manipulation and drift, can be miniaturized, and is inexpensive to fabricate. Biosensor development has been approached in many ways, frequently dependent on antibody capture of specific analytes, coupled with a luminescent output, Y. L. Cao, et al., Ultrasensitive luminol electrochemiluminescence for protein detection based on in situ generated hydrogen peroxide as coreactant with glucose oxidase anchored AuNPs@MWCNTs labeling *Biosensors & Bioelectronics*. 31(1), 305 (2012); J. Ren, et al., Increased detection of human cardiac troponin I by a decrease of nonspecific adsorption in diluted self-assembled monolayers *Appl Surf Sci.* 258(13), 5230 (2012), or electrical output. G. C. Jensen, et al., Inkjet-printed gold nanoparticle electrochemical arrays on plastic. Application to immunodetection of a cancer biomarker protein *Physical Chemistry Chemical Physics*. 13(11), 4888 (2011); C. K. Tang, et al., Fabrication of immunosensor microwell arrays from gold compact discs for detection of cancer biomarker proteins *Lab on a Chip*. 12(2), 281 (2012); Y. H. Dou, et al., Voltammetric Immunoassay for the Detection of Protein Biomarkers *Electroanalysis*. 24(2), 264 (2012); K. X. Mao, et al., Label-free electrochemical immunosensor based on graphene/methylene blue nanocomposite *Analytical Biochemistry*. 422(1), 22 (2012); and G. Lee, et al., Electrochemical detection of high-sensitivity CRP inside a microfluidic device by numerical and experimental studies *Biomedical Microdevices*. 14(2), 375 (2012).

Except for single antigen-antibody electrochemical observations, G. C. Jensen, et al., Inkjet-printed gold nanoparticle electrochemical arrays on plastic. Application to immunodetection of a cancer biomarker protein *Physical Chemistry Chemical Physics*. 13(11), 4888 (2011); Y. H. Dou, et al., Voltammetric Immunoassay for the Detection of Protein Biomarkers *Electroanalysis*. 24(2), 264 (2012); K. X. Mao, et al., Label-free electrochemical immunosensor based on graphene/methylene blue nanocomposite *Analytical Biochemistry*. 422(1), 22 (2012), these systems require complex, multistep fabrications and series of reagent exchanges and electrochemical measurements that lack binary outputs or integrated logic.

An innovation to the field is the development of FETs as biosensor platforms. FETs allow real-time sensing of analytes, binary outputs, logic functions, and signal amplification. FETs have been used to detect down to fM concentrations of analytes in solution. P. I. Reyes, et al., ZnO thin film transistor immunosensor with high sensitivity and selectivity, *Applied Physics Letters*. 98(17), 173702 (2011); S. Hideshima, et al., Fabrication of stable antibody-modified field effect transistors using electrical activation of Schiff base cross-linkages for tumor marker detection *Biosensors & Bioelectronics.* 26(5), 2419 (2011); and G. Shalev, et al., The interplay between pH sensitivity and label-free protein detection in immunologically modified nano-scaled field-effect transistor *Biosensors & Bioelectronics.* 31(1), 510 (2012).

Further, organic FET (OFET) biosensors, with organic-based semiconductors (OSCs, also encompassing sol-gel oxides and carbon nanotubes) as active thin films, are a new and advanced technology nearing commercialization for flexible, high-throughput, μm-mm-scale electronics ("plastic electronics"). A most attractive OFET application is chemical sensing, because the OSC carrier energy levels and surface binding chemistry can be precisely tuned, and analytes adsorb close to the charge transport pathways, leading to strong response signals.

Several OFET-based sensor approaches have been investigated. For example, OFETs with monolayer-thick OSCs and simple hydroxy binding groups have been shown to respond strongly and rapidly to a volatile phosphonate ester. J. Huang, et al., Hydroxy-terminated organic semiconductor-based field-effect transistors for phosphonate vapor detection *Journal of the American Chemical Society.* 129 (30), 9366 (2007); J. Huang, et al., Monolayer-dimensional 5,5'-Bis(4-hexylphenyl)-2,2'-bithiophene transistors and chemically responsive heterostructures *Advanced Materials.* 20(13), 2567 (2008); and K. C. See, et al., Enhanced response of n-channel naphthalenetetracarboxylic diimide transistors to dimethyl methylphosphonate using phenolic receptors *Advanced Materials.* 19(20), 3322 (2007).

The stable operation of an OFET in aqueous media has been reported and used to record a response to an added biochemical. T. Someya, et al., Integration and response of organic electronics with aqueous microfluidics *Langmuir.* 18(13), 5299 (2002). Since that initial report, great progress has been made to stabilize OFETs further for sensing in physiological solutions. H. U. Khan, et al., In situ, label-free DNA detection using organic transistor sensors *Adv Mater.* 22(40), 4452; H. U. Khan, et al., Pentacene Based Organic Thin Film Transistors as the Transducer for Biochemical Sensing in Aqueous Media *Chemistry of Materials.* 23(7), 1946 (2011); P. Lin and F. Yan: Organic Thin-Film Transistors for Chemical and Biological Sensing *Advanced Materials.* 24(1), 34 (2012); and L. Kergoat, et al., Advances in organic transistor-based biosensors: from organic electro-chemical transistors to electrolyte-gated organic field-effect transistors *Analytical and Bioanalytical Chemistry.* 402(5), 1813 (2012).

Responses to nM and 10 ppb concentrations have been reported. P. Lin and F. Yan: Organic Thin-Film Transistors for Chemical and Biological Sensing *Advanced Materials.* 24(1), 34 (2012). Specific medical applications of this technology, however, remain limited.

One advantageous approach couples two or more sensitive field-effect transistors (FETs) in circuits that increase the signal/noise and selectivity of the outputs, and provide additional options for quantifying marker concentrations. N. J. Tremblay, et al., Digital Inverter Amine Sensing via Synergistic Responses by n and p Organic Semiconductors *Advanced Functional Materials.* 21, (22), 4314-4319 (2011); see also International PCT Patent Application Publication No. WO/2012/006546 for "Circuits, Devices and Sensors for Fluid Detection," to Katz, et al., published Jan. 12, 2012, which is incorporated herein by reference in its entirety.

One type of sensor is a complementary inverter sensor, which uniquely combine sensitive OFETs additively and are readable by sweeping a voltage range to obtain an analog inversion voltage, or by monitoring a single input voltage for a change in digital output at a threshold analyte concentration. Multiple inverters can be arrayed, each with materials designed to trip, B. M. Dhar, et al., Threshold voltage shifting for memory and tuning in printed transistor circuits *Materials Science & Engineering R-Reports.* 72(4), 49 (2011), at a different threshold concentration so the analyte can be quantified.

B. FET Biosensor Systems and Related Methods for Detecting Analytes in Aqueous and Biological Environments The presently described subject matter provides FET biosensor systems and methods that are operable in aqueous solutions and biological samples at varied pH for detecting a variety of analytes, including biomarkers. In addition, the biosensor systems of the presently described subject matter are operable when exposed to harsh ammonia (pH 12) or HCl (pH 2.5) solutions. The biosensor systems and methods of the present disclosure have use in point-of-care medical applications as diagnostic and/or predictive tools. For example, the biosensor systems and methods are useful for detecting protein biomarkers including protein biomarkers of central nervous system injury, brain injury in children with sickle cell disease (SCD), birth asphyxia, and extracorporeal membrane oxygenation support.

One embodiment of the biosensor systems and methods of the present disclosure is described for the detection in physiological solutions of sub-nanomolar concentrations of a protein that has been shown to be a biomarker of brain injury, glial fibrillary acidic protein (GFAP). W. J. Savage, A. D. Everett, and J. F. Casella, *Plasma glial fibrillary acidic protein levels in a child with sickle cell disease and stroke*, Acta Haematol 125, 103 (2011). The biosensor system described has an anti-GFAP antibody on its surface. The biosensor system can detect GFAP in real time. The biosensor systems and methods are described in greater detail below.

FIG. 1A illustrates a diagram depicting an example biosensor system 100 operating in a process for detecting binding of an analyte of interest in accordance with embodiments of the present disclosure. In this example, the analyte of interest is a protein, although it may be any suitable type of analyte. Referring to FIG. 1A, the biosensor system 100 includes a detector 102 configured to detect a change in an electrical property. Particularly, in this example, the detector 102 is an organic field effect transistor (FET) comprising a silicon (Si) conductive substrate 104 and a silicon oxide ($SiO_2$) dielectric layer 106 disposed thereon. In this example, the $SiO_2$ layer 106 has a thickness of about 10 nm, which, in some embodiments, can be increased to at least about 60 nm, although the layer may be any suitable thickness. The FET may comprise other suitable conductive substrate and dielectric layer, such as glass coated with aluminum as conductor and aluminum oxide as dielectric, or glass coated with indium tin oxide as conductor and an insulating polymer such as crosslinked poly(vinylphenol) as dielectric.

Chromium (Cr)/gold (Au) electrodes 108 may be disposed on a top surface of the $SiO_2$ layer 106. In an example, the electrodes 108 may be thermally deposited on the $SiO_2$ layer 106 through an interdigitated mask, and subsequently the electrodes 108 may be treated with pentafluorophenyl-thiol (5% volume in ethanol for 1 hour) to form layers 110 for decreasing contact resistance. Other suitable electrode materials known in the art may be used as well, such as aluminum, silver, conducting carbon ink, and the like.

A pentacene semiconductor 112 may be disposed on the top surfaces of the SiO$_2$ layer 106 and the electrodes 108. In an example, the pentacene semiconductor 112 may be thermally evaporated on the substrate with a thickness of about 50 nm or any other suitable thickness. Other semiconductors may be used, including heterocyclic oligomer and fused ring molecular semiconductors, polymeric semiconductors, metal oxide- or sulfide-based semiconductors, amorphous silicon, carbon nanotubes, silicon nanowires, and the like.

The biosensor system 100 may include a passive layer 114 disposed on a top surface of the pentacene semiconductor 112. In this example, the passive layer 114 is an amorphous fluoropolymer. The amorphous fluoropolymer may be, for example, CYTOP® fluoropolymer, produced by Asahi Glass Co. CYTOP® is an amorphous, non-crystalline fluoropolymer having the following general formula:

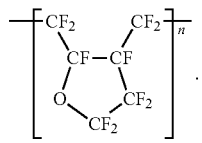

In an example, the amorphous fluoropolymer may be deposited by spin coating a 9% by weight CYTOP® solution on the top surface of the pentacene semiconductor 112. The thickness of the passive layer 114 may range, for example, between about 50 nm and about 250 nm. In the alternative, the passive layer 114 may be made of, for example, but not limited to, a perfluoroeicosane, poly-isobutylmethacrylate (PIBMA), TEFLON® derivative AF-1600, i.e., poly[4,5-difluoro-2,2-bis(trifluoromethyl)-1,3-dioxole-co-tetrafluoroethylene], having the following general formula:

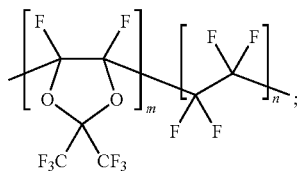

and the like.

The biosensor system 100 may include an additional hydrophobic layer 116 disposed on the passive layer 114. In this example, the hydrophobic layer may have a vapor-deposited hydrophobic material. The hydrophobic material may be a long-chain, e.g., a $C_{40}$-$C_{50}$, hydrocarbon. The long-chain hydrocarbon may have a length ranging from about 40 to about 50 carbon atoms, including 40, 41, 42, 43, 44, 45, 46, 47, 47, 49, and 50 carbon atoms. The long-chain hydrocarbon may be tetratetracontane having 44 carbons (referred to herein as "C44"). In an example, the hydrophobic layer 116 may have a thickness of about 20 nm or any suitable thickness. The thickness of the hydrophobic layer 116 may range, for example, between about 15 nm and about 20 nm. The combined passive and hydrophobic layers are preferably selected to minimize chemical and electronic leakage from the analyte solution to the semiconductor, while maximizing capacitive coupling of the electronic redistributions caused by analyte binding events to the semiconductive layer.

The biosensor system 100 may include a receptor-attachment material 118 disposed on the hydrophobic layer and configured for binding to an analyte. In an example, the receptor-attachment material 118 includes a receptor-attachment polymer having a functional group for attachment of one or more receptors 120. The receptor-attachment polymer may be one or more of a polystyrene or a CYTOP® fluoropolymer or any other suitable material. The receptor-attachment polymer may adhere to the hydrophobic layer 116 (or the passive layer 114 in the absence of the hydrophobic layer) when exposed to analyte solutions to be discussed below. The receptor-attachment polymer can be a linear, branched, or dendritic polymer. In an example, the polystyrene is polystyrene co-polyacrylic acid (PS-co-PAA). In an example, the receptor-attachment material 118 may be EDC and NHS activated PS-co-PAA (e.g., 10 mg/mL in 60% DMF and 40% DCM mix solvent) that is spin coated on the hydrophobic layer 116. The receptor-attachment material 118 may alternatively be deposited by any other suitable technique.

A wide range of receptors 120 may be attached to the receptor-attachment material for detection of a wide range of analytes. For example, a receptor may be an antigen to detect binding to the antibody analyte of interest. In another example, the receptor is a nucleic acid, such as a DNA molecule, to detect binding of the hybrid nucleic acid analyte of interest. In another example, the receptor is an enzyme to detect binding of a substrate analyte of interest or an enzyme inhibitor molecule of interest. In another example, the receptor is a RNA aptamer to detect binding to a protein analyte of interest. Example receptors 120 include, but are not limited to, an antibody, an antigen, an enzyme, a substrate, an inhibitor, a peptide, a protein, a nucleic acid, a DNA, and a RNA aptamer. More particularly, the antibody may be an antibody that binds to GFAP. More particularly, the antibody may be an antibody that binds C-reactive protein (CRP) or secretory phospholipase A2 (sPLA2). The RNA aptamer may be for specific binding to neurogranin, metallothionein III, oligodendrocyte glycoprotein, or GFAP. The advantage of RNA aptamers as receptors is they are very small (40 bases) relative to antibodies, such that the density of the aptamer relative to the biosensor surface can be increased. Example analytes include, but are not limited to, a biomarker, an antibody, a metabolite, an electrolyte, a drug, a biomarker of organ function, an organ injury biomarker protein, an organ byproduct, an organ metabolite, a brain injury biomarker, a biomarker of renal function, and a biomarker of anticoagulation.

In an example, receptor 120 may be attached to the receptor-attachment polymer through a functional group. The receptor-attachment functional group may be selected from a large number of coupling groups known in the art including, but not limited to, one or more of an aldehyde group, a hydroxyl group, a thiol group, an amino group, a carbonyl group, a carboxyl group, a vinyl group, a diene group (for Diels-Alder chemistry), an acetylenyl group, or an azide group. The acetylenyl group and the azide group can react with each other in a process known as "click chemistry." The receptor-attachment functional group may be covalently bound to the receptor-attachment polymer, or embedded within it via a side chain that is compatible with the receptor-attachment polymer. The receptor 120 may be deposited on the receptor-attachment material 118 by any suitable technique. For example, the receptor 120 may be attached to the receptor-attachment polymer through the functional group using standard chemical techniques known in the art such as, for example, via peptide coupling or click chemistry as described above, or in addition using streptavidin-biotin linkage. More than one receptor may be attached to a single functional group on the receptor-attachment material.

During operation of the biosensor, the receptor 120 may bind to an analyte 122 of interest. The binding of the analyte to the receptor causes a change of the electrical property at a surface of the detector 102 for causing detection of the presence of the analyte of interest. To detect the presence of an analyte of interest, the detector 102 may be activated by application of a negative voltage to the FET gate. A certain density of charge carriers (holes) can be generated at the interface between the semiconductor and dielectric layer, and the holes flow toward the drain electrode after application of the negative voltage between the drain and source electrodes, thus generating drain current. A certain density of charge carriers (holes) are generated at the interface between the semiconductor and dielectric layer after a negative gate voltage has been applied, and the holes flow toward the drain electrode after applying negative drain voltage between source and drain electrodes, thus generating drain current. In one example, GFAP is the analyte to be detected and the biosensor has a receptor that is an anti-GFAP antibody attached at its surface for binding to the GFAP. To detect the presence of the protein, GFAP can be introduced at the biosensor surface. GFAP is a negatively charged protein at pH 7.4, and binding of the GFAP to the receptor decreases the density of holes in the transistor channel, thus decreasing the drain current. Rinsing the GFAP can have the opposite effect on the drain current. During operation, the biosensor may be positioned in a suitable biological environment. For example, the biosensor may be placed in blood, serum, plasma, urine, cerebrospinal fluid, lymph, saliva, bile, or the like.

In accordance with embodiments, the receptors 120 may be of the same type or multiple different types of receptors. By use of different types of receptors, the system can detect the presence of multiple different types of analytes when the analytes bind to the receptors.

The biosensor system 100 may include a computing device 124 in electrical communication with the detector 102. The computing device 124 may include suitable hardware, software, and/or firmware. For example, the computing device 124 may include one or more processors and memory configured to activate the detector 102 and to receive electrical signals from the detector 102. For example, the computing device 124 may be a desktop or laptop computer with control equipment configured to detect the drain current signals from the detector 102. The computer device 124 may store data representative of the current signals in its memory and/or present the signal data to a user via user interface, such as a display. The signal data may indicate the binding of the analyte to the receptor over time. Further, the display or capture of the electrical signal may be in real time. The biosensor system 100 may include a means of delivering fluid to the biosensor.

The sensor size may be any suitable size. In an example, the sensor size is 8 mm×8 mm for making the sensor easier to produce, for example, by use of printing techniques.

FIG. 1B illustrates a diagram depicting another example biosensor system 100 in accordance with embodiments of the present disclosure. In this example, the device surface is functionalized by ethanolamine, rather than an antibody, and demonstrates the necessity of an antibody (or a receptor functional group) for selective detection of an analyte.

FIG. 2 illustrates a diagram depicting another example biosensor system 200 operating in a process for detecting binding of an analyte of interest in accordance with embodiments of the present disclosure. Referring to FIG. 2, the biosensor system 200 includes a detector 202 configured to detect a change in an electrical property. Particularly, in this example, the detector 102 the detector is an organic field effect transistor (FET) comprising a silicon (Si) substrate 204 and a silicon oxide ($SiO_2$) layer 206 disposed thereon. In this example, the $SiO_2$ layer 206 has a thickness of 10 nm, although the layer may be any suitable thickness. As an example, the $SiO_2$ layer may have a thickness between about 10 nm and about 60 nm. The detector 202 also may include a pentacene layer 208 disposed on the $SiO_2$ layer 206. Further, the detector 202 may include Au electrodes 210. In an example, the electrodes 210 may be thermally deposited on the pentacene layer 208 through an interdigitated mask.

A passive layer 212 may be deposited on top of the pentacene layer 208 and the Au electrodes 210. The passive layer 212 may be made of a CYTOP® fluoropolymer. A hydrophobic layer 214 can be deposited on top of the passive layer 212. In this example, the hydrophobic layer may include a vapor-deposited hydrophobic material. As an example, the passive layer may have a thickness between about 50 nm and about 250 nm. The hydrophobic material may include a long-chain, e.g., a $C_{40}$-$C_{50}$ hydrocarbon. The hydrophobic layer may include one or more hydrophobic polymers. The hydrophobic polymer may be a fluoropolymer, a CYTOP® fluoropolymer, poly-isobutylmethacrylate (PIBMA), TEFLON® derivative AF-1600, or the like. As an example, the hydrophobic layer may have a thickness between about 15 nm and about 20 nm. The total thickness of the layers disposed on top of the FET may range, for example, between about 66 nm and about 270 nm.

The hydrophobic layer 214 may include a receptor-attachment material configured for binding to an analyte. In an example, the receptor-attachment material is a receptor-attachment polymer having a functional group for attachment of a receptor 216. The receptor-attachment polymer may be fluoropolymer. In FIG. 2, the receptor-attachment molecule is $C_8F_{17}C_3H_6NH_2$ 3-(perfluorooctyl)propylamine. One of ordinary skill in the art would appreciate that other receptor-attachment polymers are suitable for use with the presently disclosed subject matter. Receptors 216 may be attached to the hydrophobic layer 214 in accordance with examples described herein.

In another example, two or more biosensors can be coupled in circuits that increase the signal/noise and selectivity of the outputs.

In many of the examples disclosed herein, the detector is described as being a FET, although any suitable type of detector configured to detect a change in an electrical property, such as a charge change, on its surface may be used. Example detectors include, but are not limited to, other types of transistors, laterally configured diodes, single nanowire chemiresistors, and the like. In some embodiments, the detector comprises a device selected from the group consisting of a field effect transistor, carbon nanotubes, silicon nanowires, biochem-resistor, and $SnO_2$ nanobelt.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Production of a Biosensor for Detecting Glial Fibrillary Acidic Protein (GFAP)

The structure of the field effect transistor (FET) biosensor produced for detecting GFAP is shown in FIG. 1A. First, 3-nm Cr and 50-nm Au were thermally deposited on 10-nm $SiO_2$ through an interdigitated mask, and then the Au electrodes were treated with pentafluorophenylthiol (5% volume in ethanol, 1 hour) to decrease contact resistance. Pentacene semiconductor was thermally evaporated on the substrate with a thickness of 50 nm, and then 9% by weight CYTOP® solution was spin coated on the pentacene, and 20-nm tetratetracontane was thermally evaporated on the CYTOP® as a glue layer. A hydrophilic, but not water soluble polymer, polystyrene co-polyacrylic acid, (PS-co-PAA), was first activated to allow for attachment of an analyte binding receptor and then the polymer was spin coated on tetratetracontane (C-44). In this example, the analyte binding receptor was monoclonal anti-GFAP antibody for binding the analyte GFAP. The PS-co-PAA (10-mg/mL in 60% DMF and 40% DCM mix solvent) was activated using 1-Ethyl-3-[3-dimethylaminopropyl]carbodiimide hydrochloride (EDC) and N-hydroxysuccinimide (NHS) chemistry according to procedures known in the art. For antibody attachment to the activated PS-co-PAA, an antibody solution (1-mg/mL monoclonal anti-GFAP antibody in phosphate-buffered saline (PBS)) was placed on the activated PS-co-PAA surface and reacted for 6 hours at room temperature. Unbound antibody was rinsed away with PBS, then 10% v/v ethanolamine in PBS was dropped on device surface for 6 hours at room temperature to block any unreacted activated carboxylic group.

Without wishing to be bound to any one particular theory, it is thought that the mechanism of protein sensing is as follows. A certain density of charge carriers (holes) are generated at the interface between the semiconductor and dielectric layer after a negative gate voltage has been applied, and the holes flow toward the drain electrode after applying negative drain voltage between source and drain electrodes, thus generating drain current. To detect the presence of protein, GFAP protein was introduced at the device surface having the attached anti-GFAP antibody. GFAP is a negatively charged protein at pH 7.4 PBS, and it was observed that the binding of this negatively charged layer caused a charge redistribution that appeared to decrease the density of holes in the transistor channel, thus decreasing the drain current. Rinsing the GFAP had the opposite effect on the drain current.

An alternative structure of a FET biosensor produced for detecting GFAP is shown in FIG. 2A. In this example, a pentacene FET was capped with a CYTOP® fluorinated polymer passivating layer functionalized with 3-perfluorooctylpropylamine. The same monoclonal anti-GFAP antibody described above was attached using standard EDC/NHS based peptide coupling chemistry according to methods known in the art (see schematic in FIG. 3). The device current was established with PBS on top of the biosensor surface. GFAP (0.5 µg/mL) was introduced, and a 20% current modulation was observed (FIG. 2B). This prototype biosensor confirms that the FET architecture and surface coupling chemistry can be used as a biosensor for brain injury biomarkers. The CYTOP®-pentacene interface was independently reported to be stable to water-induced current drift from bias stress. Capacitive coupling through top gate dielectrics also is well precedented.

To confirm that the antibody had been successfully attached to the biosensor surface by the EDC/NHS based bioconjugation chemistry, the anti-GFAP antibody was first labeled with rhodamine B as shown in FIG. 4. The carboxyl group was activated on the rhodamine B with EDC and NHS and the activated rhodamine B was attached to the anti-GFAP antibody by the reaction of NHS with the amine group on the antibody. The labeled antibody was then attached to the device surface by EDC/NHS based bioconjugation chemistry as described above. Orange fluorescence was observed on the device surface for the samples containing rhodamine B labeled anti-GFAP antibody with EDC/NHS activated device surface, while no fluorescence was observed for the samples containing only EDC/NHS activated rhodamine B without anti-GFAP antibody activated device surface (data not shown). Additional experiments were performed to confirm the successful attachment of antibody (data not shown).

Example 2

Real Time Detection of GFAP with a Biosensor

This experiment was performed to detect GFAP with the biosensor described above in Example 1. Typically, a drain current of a biosensor will slowly increase over time when PBS is kept on its surface due to water doping; as is consistent with previous literature. To test detection of GFAP with the biosensor described above in Example 1, 900 nM GFAP was injected on the device surface, and a fast current decrease was observed as can be seen in the graph of drain current versus time shown in FIG. 4a. Two sensing cycles were performed; in the first sensing cycle, the current first decreased then increased again, which may have been due to the device still approaching the equilibrium point due to the PBS effect (FIG. 5a). The second sensing cycle gave an improved response, as the drain current recovered immediately after replacing GFAP with PBS (FIG. 5a). This result indicated that the observed response is reversible and the device may be reusable.

To check the selectivity of the sensor, pepsin was chosen as a comparison protein due to its good availability; furthermore, in PBS solution, both GFAP and pepsin are negatively charged. As shown in the graph of drain current versus time in FIG. 5(b), pepsin PBS solution also caused some current decrease, but the magnitude of the decrease was smaller than that observed for GFAP even at a significantly higher concentration.

In the second set of experiments, a significantly lower GFAP concentration was used as the analyte provided to the device surface, as shown in the graph of drain current versus time in FIG. 6a. FIG. 6a shows that 100-nM GFAP also can give a large and reproducible response. In addition, the biosensor response to GFAP was analyzed in more complex systems, such as dilute milk (1%) and blood (1%), to simulate the use of the biosensor in a biological fluid. The response was compared in blood and milk with and without GFAP. In both systems, the protein concentration is much higher than 100 nM, however, the responses from the milk and blood solutions are still lower than the response observed for 100-nM GFAP (FIG. 5a). Use of a significantly lower concentration of GFAP (20 nM, 50 nM) also was shown to give a visible response (FIG. 6b). As shown in FIG. 6b, the response peak of 1% blood with 50-nM GFAP is higher than the response of 1% blood alone. Also shown in FIG. 6b, after injecting 20-nM GFAP into 1% blood, a bigger peak appears (shown in the circle). All of the data combined indicate that it is possible for this sensor to detect very low concentrations of GFAP in complex systems, such as milk and blood.

The thickness of the CYTOP® layer (passive layer) of the biosensor was determined to be highly important for the sensing performance. Thicker CYTOP® layers can lead to a smaller change in the drain current. The issue is that a thicker passive layer provides better protection for the semiconductor in the aqueous and/or biological environment necessary for a biosensor. A thicker CYTOP® layer was shown to improve device stability over longer time periods in PBS (data not shown). An experiment was performed with a biosensor according to Example 1 except that the CYTOP® layer was significantly thicker in this case (about 250 nm versus about 50 nm for the biosensor of Example 1). FIG. 7 shows a graph of drain current versus time when different analytes are provided to the biosensor surface. Although the current change is significantly smaller, the biosensor device still provided sufficient sensitivity and excellent selectivity.

Additional graphs of drain current versus time are shown in FIG. 8 and FIG. 9 for detection of GFAP by the biosensor described in Example 1. These experiments demonstrate that sub-nanomolar concentrations of GFAP can be detected with the biosensor. In these experiments bovine serum albumin (BSA) was used as a control to test for the selectivity of the biosensor for GFAP. In FIG. 8, 4-nM GFAP was detected at the device surface as evidenced by a large decrease in drain current, while 800-nM BSA elicited only a minor change in response. A similar result was demonstrated in response to provision of only 0.4-nM GFAP at the biosensor surface (FIG. 9).

The optimum voltage for detection of GFAP (500 ng/mL) was determined and the experimental results are shown in a graph of drain current versus voltage in the presence of PBS or GFAP (FIG. 10). FIG. 11 shows a graph of drain current versus time when GFAP is provided at the surface of the biosensor following PBS and then a subsequent PBS rinse. FIG. 11 illustrates that the current is significantly decreased at provision of GFAP and subsequently restored upon the PBS rinse.

FIG. 12 shows a graph of drain current versus time when using a lower GFAP concentration (4 ng/mL) and higher and broader BSA concentration (11 mg/mL and 100 ng/mL). FIG. 13 shows a graph of drain current versus time depicting a limit of detection of GFAP (2 ng/mL).

FIG. 14 shows a graph of drain current versus time for control sensing experiments using the system shown in FIG. 1B. As shown in FIG. 14, there are no specific interaction signals between the device surface and GFAP. When adding GFAP PBS solution on the device surface, both BSA and GFAP showed the same types of random changes. This result demonstrates the importance and evidence of specific interaction between antibody and target protein to generate a desired detection signal.

Note that currents are negative in the graphs of drain current vs. time because the currents are measured at an electrode to which a negative voltage is applied. It is changes in absolute value of current, however, that signify the responses.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

W. J. Savage, A. D. Everett, and J. F. Casella, *Plasma glial fibrillary acidic protein levels in a child with sickle cell disease and stroke*, Acta Haematol 125, 103 (2011).

W. J. Savage, E. Barron-Casella, Z. Fu, P. Dulloor, L. Williams, B. J. Crain, D. A. White, J. M. Jennings, J. E. Van Eyk, M. R. Debaun, A. Everett, and J. F. Casella, *Plasma glial fibrillary acidic protein levels in children with sickle cell disease*, Am J Hematol 86, 427 (2011).

M. M. Bembea, W. Savage, J. J. Strouse, J. M. Schwartz, E. Graham, C. B. Thompson, and A. Everett, *Glial fibrillary acidic protein as a brain injury biomarker in children undergoing extracorporeal membrane oxygenation*, Pediatr Crit. Care Med 12, 572 (2011).

L. A. Styles, C. G. Schalkwijk, A. J. Aarsman, E. P. Vichinsky, B. H. Lubin, and F. A. Kuypers, *Phospholipase A2 levels in acute chest syndrome of sickle cell disease*, Blood 87, 2573 (1996).

J. T. Naprawa, B. K. Bonsu, D. G. Goodman, and M. A. Ranalli, *Serum biomarkers for identifying acute chest syndrome among patients who have sickle cell disease and present to the emergency department*, Pediatrics 116, 2004-2107 (2005).

E. M. Bargoma, J. K. Mitsuyoshi, S. K. Larkin, L. A. Styles, F. A. Kuypers, and S. T. Test, *Serum C-reactive protein parallels secretory phospholipase A2 in sickle cell disease patients with vasoocclusive crisis or acute chest syndrome*, Blood 105, 3384 (2005).

L. A. Styles, M. Abboud, S. Larkin, M. Lo, and F. A. Kuypers, *Transfusion prevents acute chest syndrome predicted by elevated secretory phospholipase A2*, Br J Haematol 136, 343 (2007).

D. B. Andropoulos, J. V. Hunter, D. P. Nelson, S. A. Stayer, A. R. Stark, J. S. Heinle, D. E. Graves, C. D. Fraser, Jr., *Brain Immaturity is Associated with MRI Brain Injury Before and After Neonatal Cardiac Surgery with High-Flow Bypass and Cerebral Oxygenation Monitoring*, J Thorac Cardiovasc Surg. 2010 March; 139(3): 543-556.

C. S. Ennem, T. A. G. M. Huisman, W. J. Savage, F. J. Northington, J. Jennings, A. D. Everett, E. M. Graham. *Glial Fibrillary Acidic Protein as a Biomarker for Neonatal Hypoxic-Ischemic Encephalopathy Treated with Total Body Cooling*, Am J Obstet Gynecol, 205:251, (2011).

Y. L. Cao, R. Yuan, Y. Q. Chai, L. Mao, H. Niu, H. J. Liu and Y. Zhuo: Ultrasensitive luminol electrochemiluminescence for protein detection based on in situ generated hydrogen peroxide as coreactant with glucose oxidase anchored AuNPs@MWCNTs labeling *Biosensors & Bioelectronics*. 31(1), 305 (2012).

J. Ren, X. Q. Ding, J. J. Greer and K. Shankar: Increased detection of human cardiac troponin I by a decrease of nonspecific adsorption in diluted self-assembled monolayers *Appl Surf Sci.* 258(13), 5230 (2012).

G. C. Jensen, C. E. Krause, G. A. Sotzing and J. F. Rusling: Inkjet-printed gold nanoparticle electrochemical arrays on plastic. Application to immunodetection of a cancer biomarker protein *Physical Chemistry Chemical Physics.* 13(11), 4888 (2011).

C. K. Tang, A. Vaze and J. F. Rusling: Fabrication of immunosensor microwell arrays from gold compact discs for detection of cancer biomarker proteins *Lab on a Chip.* 12(2), 281 (2012).

Y. H. Dou, S. J. Haswell, J. Greenman and J. Wadhawan: Voltammetric Immunoassay for the Detection of Protein Biomarkers *Electroanalysis.* 24(2), 264 (2012).

K. X. Mao, D. Wu, Y. Li, H. M. Ma, Z. Z. Ni, H. Q. Yu, C. N. Luo, Q. Wei and B. Du: Label-free electrochemical immunosensor based on graphene/methylene blue nanocomposite *Analytical Biochemistry.* 422(1), 22 (2012).

G. Lee, I. Park, K. Kwon, T. Kwon, J. Seo, W. J. Chang, H. Nam, G. S. Cha, M. H. Choi, D. S. Yoon and S. W. Lee: Electrochemical detection of high-sensitivity CRP inside a microfluidic device by numerical and experimental studies *Biomedical Microdevices.* 14(2), 375 (2012).

P. I. Reyes, C. J. Ku, Z. Q. Duan, Y. C. Lu, A. Solanki and K. B. Lee: ZnO thin film transistor immunosensor with high sensitivity and selectivity *Applied Physics Letters.* 98(17), 173702 (2011).

S. Hideshima, R. Sato, S. Kuroiwa and T. Osaka: Fabrication of stable antibody-modified field effect transistors using electrical activation of Schiff base cross-linkages for tumor marker detection *Biosensors & Bioelectronics.* 26(5), 2419 (2011).

G. Shalev, Y. Rosenwaks and I. Levy: The interplay between pH sensitivity and label-free protein detection in immunologically modified nano-scaled field-effect transistor *Biosensors & Bioelectronics.* 31(1), 510 (2012).

J. Huang, J. Miragliotta, A. Becknell and H. E. Katz: Hydroxy-terminated organic semiconductor-based field-effect transistors for phosphonate vapor detection *Journal of the American Chemical Society.* 129(30), 9366 (2007).

J. Huang, J. Sun and H. E. Katz: Monolayer-dimensional 5,5'-Bis(4-hexylphenyl)-2,2'-bithiophene transistors and chemically responsive heterostructures *Advanced Materials.* 20(13), 2567 (2008).

K. C. See, A. Becknell, J. Miragliotta and H. E. Katz: Enhanced response of n-channel naphthalenetetracarboxylic diimide transistors to dimethyl methylphosphonate using phenolic receptors *Advanced Materials.* 19(20), 3322 (2007).

T. Someya, A. Dodabalapur, A. Gelperin, H. E. Katz and Z. Bao: Integration and response of organic electronics with aqueous microfluidics *Langmuir.* 18(13), 5299 (2002).

H. U. Khan, M. E. Roberts, O. Johnson, R. Forch, W. Knoll and Z. Bao: In situ, label-free DNA detection using organic transistor sensors *Adv Mater.* 22(40), 4452.

H. U. Khan, M. E. Roberts, W. Knoll and Z. A. Bao: Pentacene Based Organic Thin Film Transistors as the Transducer for Biochemical Sensing in Aqueous Media *Chemistry of Materials.* 23(7), 1946 (2011).

P. Lin and F. Yan: Organic Thin-Film Transistors for Chemical and Biological Sensing *Advanced Materials.* 24(1), 34 (2012).

L. Kergoat, B. Piro, M. Berggren, G. Horowitz and M. C. Pham: Advances in organic transistor-based biosensors: from organic electrochemical transistors to electrolyte-gated organic field-effect transistors *Analytical and Bioanalytical Chemistry.* 402(5), 1813 (2012).

N. J. Tremblay, B. J. Jung, P. Breysse and H. E. Katz: Digital Inverter Amine Sensing via Synergistic Responses by n and p Organic Semiconductors *Advanced Functional Materials.* 21 (22), 4314-4319 (2011).

B. M. Dhar, R. Ozgun, T. Dawidczyk, A. Andreou and H. E. Katz: Threshold voltage shifting for memory and tuning in printed transistor circuits *Materials Science & Engineering R-Reports.* 72(4), 49 (2011).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A biosensor system for detecting binding of an analyte of interest, the biosensor system comprising:
a detector configured to detect a change in an electrical property on a surface thereof;

a passive layer disposed on a top surface of the detector;
a hydrophobic layer disposed on the passive layer, wherein the hydrophobic layer comprises a material comprising one or more long-chain hydrocarbons having a length ranging from about 40 carbon atoms to about 50 carbon atoms;
a receptor-attachment material comprising one or more of a polystyrene or a CYTOP fluoropolymer disposed on the hydrophobic layer and configured for binding to an analyte; and
one or more receptors that bind to the analyte, the one or more receptors being attached to the receptor-attachment material, wherein the binding of the analyte to the one or more receptors causes the change of the electrical property at the surface.

2. The biosensor system of claim 1, wherein the detector comprises a device selected from the group consisting of a field effect transistor, carbon nanotubes, silicon nanowires, biochem-resistor, and $SnO_2$ nanobelt.

3. The biosensor system of claim 1, wherein the passive layer comprises a material selected from the group consisting of a fluoropolymer, a perfluoroeicosane, CYTOP, poly-isobutylmethacrylate (PIBMA) and poly[4,5-difluoro-2,2-bis(trifluoromethyl)-1,3-dioxole-co-tetrafluoroethylene.

4. The biosensor system of claim 1, wherein the hydrophobic layer comprises a vapor-deposited hydrophobic material.

5. The biosensor system of claim 1, wherein the hydrophobic layer comprises one or more hydrophobic polymers.

6. The biosensor system of claim 5, wherein the one or more hydrophobic polymers are selected from the group consisting of a fluoropolymer, a CYTOP fluoropolymer, poly-isobutylmethacrylate (PIBMA), and poly[4,5-difluoro-2,2-bis(trifluoromethyl)-1,3-dioxole-co-tetrafluoroethylene.

7. The biosensor system of claim 1, wherein the receptor-attachment material comprises a receptor-attachment polymer comprising a functional group for attachment of the one or more receptors.

8. The biosensor system of claim 7, wherein the receptor-attachment polymer is selected from the group consisting of a linear polymer, a branched polymer, and a dendritic polymer.

9. The biosensor system of claim 7, wherein the receptor-attachment functional group comprises one or more of an aldehyde group, a hydroxyl group, a thiol group, an amino group, a carbonyl group, a carboxyl group, a vinyl group, a diene group, an acetylenyl group, or an azide group.

10. The biosensor system of claim 1, wherein the polystyrene is polystyrene co-polyacrylic acid (PS-co-PAA).

11. The biosensor system of claim 1, wherein the thickness of the passive layer ranges from about 50 nm to about 250 nm.

12. The biosensor system of claim 1, wherein a thickness of the hydrophobic layer ranges from about 15 nm to about 20 nm.

13. The biosensor system of claim 1, wherein a total thickness of the layers ranges from about 66 nm to about 270 nm.

14. The biosensor system of claim 1, wherein the one or more receptors is selected from the group consisting of an antibody, an antigen, an enzyme, a substrate, a peptide, a protein, a nucleic acid, RNA, and a DNA.

15. The biosensor system of claim 1, wherein the analyte is selected from the group consisting of a biomarker, an antibody, a metabolite, an electrolyte, a drug, a biomarker of organ function, an organ injury biomarker protein, an organ byproduct, an organ metabolite, a brain injury biomarker, a biomarker of renal function, and a biomarker of anticoagulation.

16. The biosensor system of claim 1, wherein the analyte is glial fibrillary acidic protein (GFAP) and the one or more receptors is a GFAP antibody.

17. The biosensor system of claim 1, wherein the detector is positioned in a biological environment.

18. The biosensor system of claim 17, wherein the biological environment comprises one of blood, serum, plasma, urine, cerebrospinal fluid, lymph, saliva, and bile.

19. The biosensor system of claim 1, wherein the one or more receptors is a first receptor and the analyte is a first analyte, and
wherein the biosensor further comprises one or more second receptors each of a type different than the first receptor, wherein the one or more second receptors are attached on the receptor-attachment material for binding to one or more second analytes that are each of a type different than the first analyte.

20. The biosensor system of claim 1, wherein the detector is configured to generate an electrical signal in response to the change in the electrical property, and
wherein the method further comprises a computing device in electrical communication with the detector and configured to receive the electrical signal for indicating the binding of the analyte to the one or more receptors.

21. The biosensor system of claim 20, wherein the computing device comprises a user interface configured to indicate the binding of the analyte to the one or more receptors.

22. The biosensor system of claim 20, wherein the detector is configured to generate the electrical signal in response to the change in the electrical property in real time.

23. The biosensor system of claim 20, wherein the detector is configured to detect glial fibrillary acidic protein (GFAP) concentrations between 2 ng/mL and 4 ng/mL and to change the electrical signal in response to the detection.

24. A method for detecting binding of an analyte of interest, the method comprising:
providing a biosensor system comprising:
a detector configured to detect a change in an electrical property on a surface thereof;
a passive layer disposed on a top surface of the detector;
a hydrophobic layer disposed on the passive layer, wherein the hydrophobic layer comprises a material comprising one or more long-chain hydrocarbons having a length ranging from about 40 carbon atoms to about 50 carbon atoms;
a receptor-attachment material comprising one or more of a polystyrene or a CYTOP fluoropolymer disposed on the hydrophobic layer and configured for binding to an analyte; and
one or more receptors that bind to the analyte, the one or more receptors being attached to the receptor-attachment material, wherein the binding of the analyte to the one or more receptors causes the change of the electrical property at the surface; and
activating the detector; and
receiving an electrical signal from the detector in responding to the binding of the analyte to the one or more receptors.

25. The method of claim 24, wherein the detector comprises a device selected from the group consisting of a field effect transistor, carbon nanotubes, silicon nanowires, biochem-resistor, and $SnO_2$ nanobelt.

26. The method of claim 24, wherein the passive layer comprises a material selected from the group consisting of a fluoropolymer, a perfluoroeicosane, CYTOP, poly-isobutylmethacrylate (PIBMA) and poly[4,5-difluoro-2,2-bis(trifluoromethyl)-1,3-dioxole-co-tetrafluoroethylene.

27. The method of claim 24, wherein the hydrophobic layer comprises a vapor-deposited hydrophobic material.

28. The method of claim 24, wherein the hydrophobic layer comprises one or more hydrophobic polymers.

29. The method of claim 28, wherein the one or more hydrophobic polymers are selected from the group consisting of a fluoropolymer, a CYTOP fluoropolymer, poly-isobutylmethacrylate (PIBMA), and poly[4,5-difluoro-2,2-bis(trifluoromethyl)-1,3-dioxole-co-tetrafluoroethylene.

30. The method of claim 24, wherein the receptor-attachment material comprises a receptor polymer and a receptor-attachment functional group for attachment of the one or more receptors.

31. The method of claim 30, wherein the receptor-attachment functional group comprises one or more of an aldehyde group, a hydroxyl group, a thiol group, an amino group, a carbonyl group, a carboxyl group, a vinyl group, a diene group, an acetylenyl group, or an azide group.

32. The method of claim 24, wherein the polystyrene is polystyrene co-polyacrylic acid (PS-co-PAA).

33. The method of claim 24, wherein the thickness of the passive layer ranges from about 50 nm to about 250 nm.

34. The method of claim 24, wherein a thickness of the hydrophobic layer ranges from about 15 nm to about 20 nm.

35. The method of claim 24, wherein a total thickness of the layers ranges from about 66 nm to about 270 nm.

36. The method of claim 24, wherein the one or more receptors is selected from the group consisting of an antibody, an antigen, an enzyme, a substrate, a peptide, a protein, a nucleic acid, RNA, and a DNA.

37. The method of claim 24, wherein the analyte is selected from the group consisting of a biomarker, an antibody, a metabolite, an electrolyte, a drug, a biomarker of organ function, an organ injury biomarker protein, an organ byproduct, an organ metabolite, a brain injury biomarker, a biomarker of renal function, and a biomarker of anticoagulation.

38. The method of claim 24, wherein the analyte is glial fibrillary acidic protein (GFAP) and the one or more receptors is a GFAP antibody.

39. The method of claim 24, further comprising positioning the biosensor in a biological environment.

40. The method of claim 39, wherein positioning the biosensor comprises positioning the biosensor in one of blood, serum, plasma, urine, cerebrospinal fluid, lymph, saliva, and bile.

41. The method of claim 24, wherein the one or more receptors is a first receptor and the analyte is a first analyte, and
wherein the biosensor further comprises one or more second receptors each of a type different than the first receptor, wherein the one or more second receptors are attached on the receptor-attachment material for binding to one or more second analytes that are each of a type different than the first analyte.

42. The method of claim 24, further comprising:
activating the detector;
generating, by the detector, an electrical signal in response to the change in the electrical property;
providing a computing device in electrical communication with the detector; and
receiving the electrical signal at the computing device for indicating the binding of the analyte to the one or more receptors.

43. The method of claim 42, wherein the computing device comprises a user interface configured to indicate the binding of the analyte to the one or more receptors.

44. The method of claim 42, detecting, by the detector, glial fibrillary acidic protein (GFAP) concentrations between 2 ng/mL and 4 ng/mL, and
changing the electrical signal in response to the detection.

45. A method for manufacturing a biosensor, the method comprising:
providing a detector configured to detect a change in an electrical property on a surface thereof;
disposing a passive layer on a top surface of the detector;
disposing a hydrophobic layer on the passive layer, wherein the hydrophobic layer comprises a material comprising one or more long-chain hydrocarbons having a length ranging from about 40 carbon atoms to about 50 carbon atoms;
disposing a receptor-attachment material comprising one or more of a polystyrene or a CYTOP fluoropolymer on the hydrophobic layer, the receptor-material being configured for binding to an analyte; and
attaching one or more receptors to the receptor-attachment material, wherein the one or more receptors being configured to bind to the analyte such that the electrical property at the surface changes.

46. The method of claim 45, wherein the detector comprises a device selected from the group consisting of a field effect transistor, carbon nanotubes, silicon nanowires, biochem-resistor, and $SnO_2$ nanobelt.

47. The method of claim 45, wherein the passive layer comprises a material selected from the group consisting of a fluoropolymer, a perfluoroeicosane, CYTOP, poly-isobutylmethacrylate (PIBMA) and poly[4,5-difluoro-2,2-bis(trifluoromethyl)-1,3-dioxole-co-tetrafluoroethylene.

48. The method of claim 45, wherein the hydrophobic layer comprises a vapor-deposited hydrophobic material.

49. The method of claim 45, wherein the hydrophobic layer comprises one or more hydrophobic polymers.

50. The method of claim 49, wherein the one or more hydrophobic polymers are selected from the group consisting of a fluoropolymer, a CYTOP fluoropolymer, poly-isobutylmethacrylate (PIBMA), and poly[4,5-difluoro-2,2-bis(trifluoromethyl)-1,3-dioxole-co-tetrafluoroethylene.

51. The method of claim 45, wherein the receptor-attachment material comprises a receptor polymer and a receptor-attachment functional group for attachment of the one or more receptors.

52. The method of claim 51, wherein the receptor-attachment functional group comprises one or more of an aldehyde group, a hydroxyl group, a thiol group, an amino group, a carbonyl group, a carboxyl group, a vinyl group, a diene group, an acetylenyl group, or an azide group.

53. The method of claim 45, wherein the polystyrene is polystyrene co-polyacrylic acid (PS-co-PAA).

54. The method of claim 45, wherein the thickness of the passive layer ranges from about 50 nm to about 250 nm.

55. The method of claim 45, wherein a thickness of the hydrophobic layer ranges from 15 about nm to about 20 nm.

56. The method of claim 45 wherein a total thickness of the layers ranges from about 66 nm to about 270 nm.

57. The method of claim 45, wherein the one or more receptors is selected from the group consisting of an antibody, an antigen, an enzyme, a substrate, a peptide, a protein, a nucleic acid, RNA, and a DNA.

58. The method of claim 45, wherein the analyte is selected from the group consisting of a biomarker, an antibody, a metabolite, an electrolyte, a drug, a biomarker of organ function, an organ injury biomarker protein, an organ byproduct, an organ metabolite, a brain injury biomarker, a biomarker of renal function, and a biomarker of anticoagulation.

59. The method of claim 45, wherein the analyte is glial fibrillary acidic protein (GFAP) and the one or more receptors is a GFAP antibody.

60. The method of claim 45, further comprising positioning the biosensor in a biological environment.

61. The method of claim 60, wherein positioning the biosensor comprises positioning the biosensor in one of blood, serum, plasma, urine, cerebrospinal fluid, lymph, saliva, and bile.

62. The method of claim 45, wherein the one or more receptors is a first receptor and the analyte is a first analyte, and wherein the biosensor further comprises one or more second receptors each of a type different than the first receptor, wherein the one or more second receptors are attached on the receptor-attachment material for binding to one or more second analytes that are each of a type different than the first analyte.

* * * * *